(12) United States Patent
Murotani et al.

(10) Patent No.: US 9,540,404 B2
(45) Date of Patent: Jan. 10, 2017

(54) FLUORINATED ETHER COMPOUND, FLUORINATED ETHER COMPOSITION AND COATING LIQUID, AND SUBSTRATE HAVING SURFACE-TREATED LAYER AND METHOD FOR ITS PRODUCTION

(71) Applicant: ASAHI GLASS COMPANY, LIMITED, Chiyoda-ku (JP)

(72) Inventors: Eisuke Murotani, Tokyo (JP); Taiki Hoshino, Tokyo (JP); Akinobu Kunimoto, Tokyo (JP); Daisuke Jomuta, Tokyo (JP); Nobuyuki Otozawa, Tokyo (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 315 days.

(21) Appl. No.: 14/311,948

(22) Filed: Jun. 23, 2014

(65) Prior Publication Data
US 2014/0302332 A1    Oct. 9, 2014

Related U.S. Application Data

(63) Continuation of application No. PCT/JP2013/052943, filed on Feb. 7, 2013.

(30) Foreign Application Priority Data

Feb. 17, 2012  (JP) .................. 2012-032784
Oct. 9, 2012   (JP) .................. 2012-224262

(51) Int. Cl.
| | | |
|---|---|---|
| *B05D 1/02* | (2006.01) | |
| *B05D 1/18* | (2006.01) | |
| *B05D 1/28* | (2006.01) | |
| *B05D 1/30* | (2006.01) | |
| *C03C 17/30* | (2006.01) | |
| *C07F 7/18* | (2006.01) | |
| *C08G 65/00* | (2006.01) | |
| *C08G 65/336* | (2006.01) | |
| *C09D 201/10* | (2006.01) | |
| *C23C 14/12* | (2006.01) | |
| *C09K 3/18* | (2006.01) | |
| *B05D 1/00* | (2006.01) | |
| *B05D 1/20* | (2006.01) | |
| *C09D 7/12* | (2006.01) | |
| *C23C 14/06* | (2006.01) | |
| *C09D 171/00* | (2006.01) | |
| *C03C 17/32* | (2006.01) | |

(52) U.S. Cl.
CPC ............. *C07F 7/1836* (2013.01); *B05D 1/005* (2013.01); *B05D 1/02* (2013.01); *B05D 1/18* (2013.01); *B05D 1/204* (2013.01); *B05D 1/28* (2013.01); *B05D 1/30* (2013.01); *C03C 17/328* (2013.01); *C08G 65/007* (2013.01); *C08G 65/336* (2013.01); *C09D 7/1233* (2013.01); *C09D 171/00* (2013.01); *C09K 3/18* (2013.01); *C23C 14/06* (2013.01); *C03C 17/30* (2013.01); *C03C 2217/76* (2013.01); *C07F 7/18* (2013.01); *C08G 2650/48* (2013.01); *C09D 201/10* (2013.01); *C23C 14/12* (2013.01); *Y10T 428/31663* (2015.04)

(58) Field of Classification Search
CPC ........................................ C07F 7/18–7/1864
See application file for complete search history.

(56) References Cited

U.S. PATENT DOCUMENTS

| | | |
|---|---|---|
| 3,847,978 A | 11/1974 | Sianesi et al. |
| 2008/0050600 A1 | 2/2008 | Fan et al. |
| 2009/0208728 A1* | 8/2009 | Itami ................ C07F 7/1836 428/318.4 |

(Continued)

FOREIGN PATENT DOCUMENTS

| | | |
|---|---|---|
| CN | 102265360 A | 11/2011 |
| JP | 2874715 | 1/1999 |

(Continued)

OTHER PUBLICATIONS

International Search Report issued Apr. 23, 2013 in PCT/JP2013/052943 filed Feb. 7, 2013.
U.S. Appl. No. 14/221,609, filed Mar. 21, 2014, Hoshino.
U.S. Appl. No. 14/298,643, filed Jun. 6, 2014, Murotani, et al.
U.S. Appl. No. 14/298,267, filed Jun. 6, 2014, Murotani, et al.

*Primary Examiner* — Ramsey Zacharia
(74) *Attorney, Agent, or Firm* — Oblon, McClelland, Maier & Neustadt, L.L.P.

(57) ABSTRACT

To provide a fluorinated ether compound, a fluorinated ether composition and a coating liquid, whereby it is possible to form a surface-treated layer which has high initial water/oil repellency and which is excellent in abrasion resistance and fingerprint stain removability, and a substrate having a surface-treated layer and a method for its production.

A fluorinated ether compound which has a poly(oxyperfluoroalkylene) chain $((\alpha\beta)_n)$ made of at least two units $(\alpha\beta)$ linked to one another, and which has a hydrolysable silyl group on at least one terminal of the chain $((\alpha\beta)_n)$ via a linking group, wherein each unit $(\alpha\beta)$ is a poly(oxyperfluoroalkylene) group comprising one to three groups $(\alpha)$ made of at least one type of a $C_{1-2}$ oxyperfluoroalkylene group and one to three groups $(\beta)$ made of at least one type of a $C_{3-6}$ oxyperfluoroalkylene group.

16 Claims, No Drawings

(56) References Cited

U.S. PATENT DOCUMENTS

2010/0272910 A1* 10/2010 Kishita ............... C09D 183/04
427/387
2013/0004780 A1* 1/2013 Hervieu ............... C09D 5/006
428/447

FOREIGN PATENT DOCUMENTS

| | | |
|---|---|---|
| JP | 11-29585 | 2/1999 |
| JP | 2000-144097 | 5/2000 |
| JP | 2002-506887 | 3/2002 |
| JP | 2003-202960 A | 7/2003 |
| JP | 2005-508420 A | 3/2005 |
| JP | 4138936 | 6/2008 |
| JP | 2008-534696 | 8/2008 |
| JP | 2010-502784 | 1/2010 |
| JP | 2010-522758 A | 7/2010 |
| JP | 2010-254832 | 11/2010 |
| WO | 2011/059430 | 5/2011 |
| WO | 2011/060047 | 5/2011 |
| WO | WO 2012/148537 A1 | 11/2012 |

* cited by examiner

FLUORINATED ETHER COMPOUND, FLUORINATED ETHER COMPOSITION AND COATING LIQUID, AND SUBSTRATE HAVING SURFACE-TREATED LAYER AND METHOD FOR ITS PRODUCTION

TECHNICAL FIELD

The present invention relates to a fluorinated ether compound, a fluorinated ether composition or a coating liquid containing such a fluorinated ether compound, which is useful for surface treatment to impart water/oil repellency to a substrate surface. The present invention relates also to a method for producing a substrate having a surface-treated layer by using such a compound, a fluorinated ether composition or a coating liquid, and a substrate having a surface-treated layer produced by such a method.

BACKGROUND ART

A fluorinated compound is useful as a surface treating agent since it has high lubricity, water/oil repellency, etc. By imparting water/oil repellency to a substrate surface by such a surface treating agent, stains on the substrate surface will easily be wiped off, and stain removability will be improved. Among such fluorinated compounds, a fluorinated ether compound having a poly(oxyperfluoroalkylene) chain in which an ether bond (—O—) is present in the middle of a perfluoroalkyl chain is particularly excellent in the fat and oil stain removability.

A surface treating agent containing such a fluorinated ether compound is useful in applications wherein it is desired to maintain a performance (abrasion resistance) whereby the water/oil repellency is less likely to be reduced even if repeatedly rubbed by fingers, and a performance (fingerprint stain removability) whereby fingerprints deposited on a surface can easily be removed by wiping, for a long period of time, e.g. as a surface treating agent for a member constituting a surface to be touched by a finger, of a touch panel.

As such fluorinated ether compounds, specifically, fluorinated ether compounds of the following (1) to (4) are known.

(1) A fluorinated ether compound having a structure wherein ($CF_2O$) and ($CF_2CF_2O$) are randomly linked, and having a hydrolysable silyl group at a terminal (Patent Document 1)

(2) A fluorinated ether compound having a structure wherein at least two types selected from the group consisting of ($CF_2O$), ($CF_2CF_2O$), ($CF_2CF_2CF_2O$) and ($CF(CF_3)CF_2O$) are randomly linked, and having a hydrolysable silyl group at a terminal (Patent Documents 2 to 5)

(3) A fluorinated ether compound having a structure wherein only ($CF_2CF_2CF_2O$) or ($CF(CF_3)CF_2O$) is linked, and having a hydrolysable silyl group at a terminal (Patent Documents 6 and 7)

(4) A fluorinated ether compound having a structure wherein only ($CF_2CF_2CF_2CF_2O$) is linked, and having a hydrolysable silyl group at a terminal (Patent Document 8)

PRIOR ART DOCUMENTS

Patent Documents

Patent Document 1: Japanese Patent No. 4,138,936
Patent Document 2: JP-A-2008-534696
Patent Document 3: WO2011/060047
Patent Document 4: WO2011/059430
Patent Document 5: Japanese Patent No. 2,874,715
Patent Document 6: JP-A-2000-144097
Patent Document 7: JP-A-11-029585
Patent Document 8: JP-A-2002-506887

DISCLOSURE OF INVENTION

Technical Problem

According to findings by the present inventor, the fluorinated ether compound of (1) is relatively good in abrasion resistance and fingerprint stain removability, but is sometimes inadequate in water/oil repellency at the initial stage before repeated abrasion.

The fluorinated ether compound of (2) is improved in water/oil repellency at the initial stage as compared with the fluorinated ether compound of (1), but is still sometimes inadequate, and in abrasion resistance and fingerprint stain removability, it is inferior to the fluorinated ether compound of (1).

The fluorinated ether compounds of (3) and (4) are excellent in water/oil repellency at the initial stage, but are inadequate in abrasion resistance and fingerprint stain removability.

It is an object of the present invention to provide a fluorinated ether compound, a fluorinated ether composition and a coating liquid, containing the fluorinated ether compound, whereby it is possible to form a surface-treated layer having high initial water/oil repellency and being excellent in abrasion resistance and fingerprint stain removability.

It is also an object to provide a substrate having a surface-treated layer having high initial water/oil repellency and being excellent in abrasion resistance and fingerprint stain removability, and a method for its production.

Solution to Problem

The present invention provides a fluorinated ether compound, a fluorinated ether composition and a coating liquid, and a substrate having a surface-treated layer and a method for its production, with the following constructions [1] to [15].

[1] A fluorinated ether compound which has a poly(oxyperfluoroalkylene) chain made of at least two units linked to one another, and which has a hydrolysable silyl group on at least one terminal of the poly(oxyperfluoroalkylene) chain via a linking group, wherein each unit is a poly(oxyperfluoroalkylene) group comprising one to three groups (α) made of at least one type of a $C_{1-2}$ oxyperfluoroalkylene group and one to three groups (β) made of at least one type of a $C_{3-6}$ oxyperfluoroalkylene group.

[2] The fluorinated ether compound according to [1], wherein the groups (α) and (β) are arranged so that in each unit, one end is the group (α) and the other end is the group (β).

[3] The fluorinated ether compound according to [1] or [2], wherein a $C_{1-6}$ perfluoroalkyl group, or a $C_{2-6}$ perfluoroalkyl group having an etheric oxygen atom, is bonded via an oxygen atom to the carbon atom at one end of the poly(oxyperfluoroalkylene) chain, and the hydrolysable silyl group is bonded via the linking group to the oxygen atom at the other end of the poly(oxyperfluoroalkylene) chain.

[4] The fluorinated ether compound according to [3], wherein the carbon atom at one end of the poly(oxyperfluoroalkylene) chain is a carbon atom of the group (α), and the oxygen atom at the other end of the poly(oxyperfluoroalkylene) chain is an oxygen atom of the group (β).

[5] The fluorinated ether compound according to any one of [1] to [4], which has a number average molecular weight of from 2,000 to 10,000.

[6] The fluorinated ether compound according to any one of [1] to [5], wherein the group (β) is ($CF_2CF_2CF_2CF_2O$).

[7] A fluorinated ether composition containing at least 95 mass % of the fluorinated ether compound as defined in any one of [1] to [6].

[8] A coating liquid comprising the fluorinated ether compound as defined in any one of [1] to [6], and a medium.

[9] The coating liquid according to [8], wherein the medium contains at least one organic solvent selected from the group consisting of a fluorinated alkane, a fluorinated aromatic compound and a fluoroalkyl ether.

[10] A method for producing a substrate having a surface-treated layer, which comprises a step of applying the fluorinated ether compound as defined in any one of [1] to [6] or the fluorinated ether composition as defined in [7] to the surface of a substrate by vacuum deposition.

[11] A method for producing a substrate having a surface-treated layer, which comprises a step of applying the coating liquid as defined in [8] or [9] to the surface of a substrate, followed by dying.

[12] The method for producing a substrate having a surface-treated layer according to [11], wherein the method of applying the coating liquid to the surface of the substrate is a spin coating method, a wipe coating method, a spray coating method, a squeegee coating method, a dip coating method, a die coating method, an ink jet method, a flow coating method, a roll coating method, a casting method, a Langmuir-Blodgett method or a gravure coating method.

[13] The method for producing a substrate having a surface-treated layer according to any one of [10] to [12], wherein the material for the substrate is a metal, a resin, glass, a ceramic or a composite material thereof.

[14] A substrate having a surface-treated layer, obtained by treatment with the fluorinated ether composition as defined in [7].

[15] A touch panel having, on its input screen, the substrate having a surface-treated layer, obtained by treatment with the fluorinated ether composition as defined in [7].

Advantageous Effects of Invention

By the fluorinated ether compound, the fluorinated ether composition and the coating liquid, containing the fluorinated ether compound, of the present invention, it is possible to form a surface-treated layer having high initial water/oil repellency and being excellent in abrasion resistance and fingerprint stain removability.

The substrate having a surface-treated layer of the present invention has a surface-treated layer having high initial water/oil repellency and being excellent in abrasion resistance and fingerprint stain removability.

According to the method for producing a substrate having a surface-treated layer of the present invention, it is possible to produce a substrate having a surface-treated layer having high initial water/oil repellency and being excellent in abrasion resistance and fingerprint stain removability.

DESCRIPTION OF EMBODIMENTS

In this specification, a compound represented by the formula (1) will be referred to as a compound (1). Compounds and precursors represented by other formulae will be referred to in the same manner.

In the present invention, a unit being a poly(oxyperfluoroalkylene) group having groups (α) and (β) will hereinafter be referred to as a "unit (αβ)". Further, a poly(oxyperfluoroalkylene) chain made of at least two such units (αβ) linked to one another, will hereinafter be referred to as a "chain $((αβ)_n)$".

In the present invention, the main chain is a linear molecular chain whereby all molecular chains other than the main chain would be deemed to be side chains.

In the present invention, a hydrolysable silyl group is a group capable of forming a silanol group (Si—OH) when hydrolyzed. For example, —$SiL_mR_{3-m}$ in the formula (1) may be mentioned.

In the present invention, an etheric oxygen atom is an oxygen atom to form an ether bond (—O—) between carbon-carbon atoms.

In the present invention, a linking group is a group to link a chain $((αβ)_n)$ and a hydrolysable silyl group, and is, for example, a group having —$SiL_mR_{3-m}$ excluded from B in the formula (1), and such a group itself may have other oxyperfluoroalkylene group not belonging to the above chain $((αβ)_n)$.

In the present invention, the number average molecular weight of a fluorinated ether compound is calculated by the following method using a NMR analysis.

It is calculated by obtaining the number (average value) of oxyperfluoroalkylene groups by using a terminal group as a standard, by means of $^1$H-NMR (solvent: deuterated acetone, internal standard: TMS) and $^{19}$F-NMR (solvent: deuterated acetone, internal standard: $CFCl_3$). The terminal group is, for example, A or B in the formula (1).

In the present invention, a chemical formula of an oxyperfluoroalkylene group shall be presented so that its oxygen atom be on the right-hand side of the perfluoroalkylene group. A poly(oxyperfluoroalkylene) group being a unit (αβ) having groups (α) and (β) is a linear bivalent group, wherein one of the two terminals is a connecting bond bonded to a carbon atom (the carbon atom having this connecting bond will be referred to as a terminal carbon atom) and the other is a connecting bond of an oxygen atom (the oxygen atom having this connecting bond will be referred to as a terminal oxygen bond). A chemical formula of a poly(oxyperfluoroalkylene) chain being a chain $((αβ)_n)$ made of at least two units (αβ) linked to one another, shall also be presented so that the terminal oxygen atom be on the right-hand side.

In the present invention, a surface-treated layer is a layer to be formed on the surface of a substrate, by surface treatment of the substrate with the fluorinated ether compound, the fluorinated ether composition or the coating liquid of the present invention.

[Fluorinated Ether Compound]

The fluorinated ether compound of the present invention (hereinafter referred to as the present compound) is a compound which has a chain $((αβ)_n)$ made of at least two units (αβ) linked to one another, and which has a hydrolysable silyl group on at least one terminal of the chain $((αβ)_n)$ via a linking group, wherein each unit is a unit (αβ) comprising one to three groups (α) made of at least one type of a $C_{1-2}$ oxyperfluoroalkylene group and one to three groups (β) made of at least one type of a $C_{3-6}$ oxyperfluoroalkylene group.

The present compound has a hydrolysable silyl group on at least one terminal of the chain $((αβ)_n)$ via a linking group. The chain $((αβ)_n)$ is present preferably in the main chain. The number of hydrolysable silyl groups bonded to a linking group may be two or more, and is preferably from 1 to 3, more preferably 1 or 2, particularly preferably 1. The linking group is a polyvalent group having one connecting bond bonded to the chain $((\alpha\beta)_n)$ side and at least one connecting bond bonded to a silicon atom in the hydrolysable silyl group, and in a case where the number of hydrolysable silyl groups bonded to the linking group is 1, the linking group is a bivalent group. The connecting bond of the linking group bonded to the chain $((\alpha\beta)_n)$ side, is a connecting bond of a carbon atom when the linking group is bonded to a terminal oxygen atom of the chain $((\alpha\beta)_n)$ and is a connecting bond of an oxygen atom when the linking group is bonded to a terminal carbon atom of the chain $((\alpha\beta)_n)$. The connecting bond of the linking group bonded to a silicon atom of a hydrolysable silyl group is a connecting bond of a carbon atom.

In a case where the present compound does not have a hydrolysable silyl group via a linking group at one terminal of the chain $((\alpha\beta)_n)$, it has a monovalent organic group at that terminal. In a case where a monovalent organic group is bonded to a terminal carbon atom of the chain $((\alpha\beta)_n)$, it is bonded via an oxygen atom. As such an organic group, a perfluoroalkyl group or a perfluoroalkyl group having an etheric oxygen atom is preferred.

The present compound may have other oxyperfluoroalkylene group not belonging to the chain $((\alpha\beta)_n)$.

The present compound may have a hydrolysable silyl group via a linking group at one terminal of the chain $((\alpha\beta)_n)$, or may have a hydrolysable silyl group via a linking group at each terminal of the chain $((\alpha\beta)_n)$. With a view to sufficiently imparting abrasion resistance to the surface-treated layer, it preferably has a hydrolysable silyl group only at one terminal of the chain $((\alpha\beta)_n)$.

The present compound may be a single compound or a mixture of two or more types different in the chain $((\alpha\beta)_n)$, the terminal group, the linking group, etc.

In a case where two or more groups $(\alpha)$ are present in a unit $(\alpha\beta)$, the groups $(\alpha)$ in the unit $(\alpha\beta)$ may be constituted solely by one type of an oxyperfluoroalkylene group having the same number of carbon atoms, or may be constituted by two types of oxyperfluoroalkylene groups different in the number of carbon atoms.

In a case where two or more groups $(\beta)$ are present in a unit $(\alpha\beta)$, the groups $(\beta)$ in the unit $(\alpha\beta)$ may be constituted solely by one type of an oxyperfluoroalkylene group having the same number of carbon atoms, or may be constituted by at least two types of oxyperfluoroalkylene groups different in the number of carbon atoms.

The group $(\beta)$ is preferably one having $(CF_2CF_2CF_2CF_2O)$, with a view to imparting sufficiently high initial water/oil repellency to the surface-treated layer.

The total number of groups $(\alpha)$ and $(\beta)$ in a unit $(\alpha\beta)$ is preferably from 2 to 4, particularly preferably 2 or 3. In a case where the total number of groups $(\alpha)$ and $(\beta)$ in a unit $(\alpha\beta)$ is 3, two groups among them may be either ones, but are preferably two groups $(\beta)$.

The order of groups $(\alpha)$ and $(\beta)$ in a unit $(\alpha\beta)$ is not particularly limited. For example, in a case where two groups $(\alpha)$ are present, the two groups $(\alpha)$ may be linked directly, or may be bonded via at least one group $(\beta)$. In a case where the total number of groups $(\alpha)$ and $(\beta)$ in a unit $(\alpha\beta)$ is at least 3, it is preferred that one end in the unit $(\alpha\beta)$ is a group $(\alpha)$ and the other end is a group $(\beta)$. That is, in a unit $(\alpha\beta)$, groups $(\alpha)$ and $(\beta)$ are arranged preferably so that one end is a group $(\alpha)$ and the other end is a group $(\beta)$.

As the present compound has group(s) $(\alpha)$, it is possible to impart excellent abrasion resistance and fingerprint stain removability to the surface-treated layer. Further, as it has group(s) $(\beta)$, it is possible to impart high initial water/oil repellency to the surface-treated layer.

The present compound has a chain $((\alpha\beta)_n)$ made of at least two units $(\alpha\beta)$ linked to one another. In a case where one end of a unit $(\alpha\beta)$ is a group $(\alpha)$ and the other end is a group $(\beta)$, as the chain $((\alpha\beta)_n)$, it is preferred that at least two units $(\alpha\beta)$ are linked so that a group $(\alpha)$ and a group $(\beta)$ are alternately arranged between adjacent units. That is, it is preferred that the adjacent units $(\alpha\beta)$ are bonded so as to constitute a head-to-tail structure. When a group $(\alpha)$ and a group $(\beta)$ are alternately arranged between adjacent units, it becomes possible to effectively exhibit both the characteristics attributable to the group $(\alpha)$ and the characteristics attributable to the group $(\beta)$. That is, the initial water/oil repellency, the abrasion resistance and the fingerprint stain removability will be excellent.

The present compound is preferably a compound wherein to a carbon atom at one end of the chain $((\alpha\beta)_n)$, a $C_{1-6}$ perfluoroalkyl group, or a $C_{2-6}$ perfluoroalkyl group having an etheric oxygen atom, is bonded via an oxygen atom, and to an oxygen atom at the other end of the chain $((\alpha\beta)_n)$, a hydrolysable silyl group is bonded via a linking group. By such a construction, the initial water/oil repellency, the abrasion resistance and the fingerprint stain removability at the surface-treated layer will be further improved.

When the present compound has a perfluoroalkyl group at its terminal, the initial water/oil repellency at the surface-treated layer will be further improved.

The present compound is preferably a compound wherein in the units $(\alpha\beta)$, the side close to the perfluoroalkyl group is a group $(\alpha)$ and the side close to the hydrolysable silyl group is a group $(\beta)$. By such a construction, the initial water/oil repellency, the abrasion resistance and the fingerprint stain removability at the surface-treated layer will be further improved. The reason is considered to be such that groups $(\alpha)$ to impart the abrasion resistance and the fingerprint stain removability to the surface-treated layer, may thereby be present at a position close to the surface of the surface-treated layer.

The number average molecular weight of the present compound is preferably from 2,000 to 10,000. When the number average molecular weight is within such a range, the present compound is excellent in the abrasion resistance. The number average molecular weight of the present compound is more preferably from 2,100 to 9,000, particularly preferably from 2,400 to 8,000.

Usually, it is considered that with a fluorinated ether compound, the chemical bond to a substrate becomes strong as the number average molecular weight decreases. The reason is considered to be such that the number of hydrolysable silyl groups increases per unit molecular weight. However, the present inventors have confirmed that if the number average molecular weight is less than the lower limit value within the above range, the abrasion resistance is likely to decrease. Further, if the number average molecular weight exceeds the upper limit value within the above range, the abrasion resistance decreases. The reason is considered to be such that the influence due to a decrease in the number of hydrolysable silyl groups present per unit molecular weight tends to be large.

The present compound has a poly(oxyperfluoroalkylene) chain, whereby the content of fluorine atoms is large. Further, as mentioned above, at least two units $(\alpha\beta)$ wherein a group $(\alpha)$ to impart abrasion resistance and fingerprint stain removability to the surface-treated layer and a group $(\beta)$ to impart high initial water/oil repellency to the surface-treated layer are linked, are linked so that the group (α) and the group (β) are alternately arranged. Therefore, the present compound is capable of forming a surface-treated layer having high initial water/oil repellency and being excellent in abrasion resistance and fingerprint stain removability.

In surface treatment with the present compound, the fluorinated ether composition or the coating liquid, as described later, silanol groups (Si—OH) will be formed by a hydrolytic reaction of hydrolysable silyl groups (—SiL$_m$R$_{3-m}$) in the present compound, and such silanol groups will be intermolecularly reacted to form Si—O—Si bonds, or such silanol groups will undergo a dehydration-condensation reaction with hydroxy groups (substrate-OH) at the surface of a substrate to form chemical bonds (substrate-O—Si). That is, the surface-treated layer in the present invention contains the present compound in such a state that some or all of hydrolysable silyl groups in the present compound are hydrolyzed.

(Compound (1))

A preferred embodiment of the present compound is specifically represented by the following formula (1).

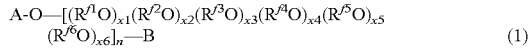

$$A—O—[(R^{f1}O)_{x1}(R^{f2}O)_{x2}(R^{f3}O)_{x3}(R^{f4}O)_{x4}(R^{f5}O)_{x5}(R^{f6}O)_{x6}]_n—B \quad (1)$$

Here, the symbols in the formula (1) are as follows.

n: an integer of at least 2
x1 and x2: each independently is an integer of from 0 to 3, and x1+x2 is an integer of from 1 to 3.
x3 to x6: each independently is an integer of from 0 to 3, and x3+x4+x5+x6 is an integer of from 1 to 3.
R$^{f1}$: a C$_1$ perfluoroalkylene group
R$^{f2}$: a C$_2$ perfluoroalkylene group
R$^{f3}$: a C$_3$ perfluoroalkylene group
R$^{f4}$: a C$_4$ perfluoroalkylene group
R$^{f5}$: a C$_5$ perfluoroalkylene group
R$^{f6}$: a C$_6$ perfluoroalkylene group
A: a C$_{1-6}$ perfluoroalkyl group, a C$_{2-6}$ perfluoroalkyl group having an etheric oxygen atom, or B
B: a group represented by one of the following formulae (2-1) to (2-5)

$$—R^{f7}CX_2O(CH_2)_3—SiL_mR_{3-m} \quad (2\text{-}1)$$

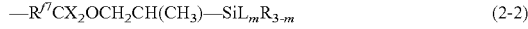

$$—R^{f7}CX_2OCH_2CH(CH_3)—SiL_mR_{3-m} \quad (2\text{-}2)$$

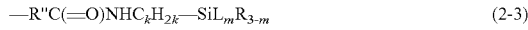

$$—R''C(=O)NHC_kH_{2k}—SiL_mR_{3-m} \quad (2\text{-}3)$$

$$—R^{f7}(CH_2)_2—SiL_mR_{3-m} \quad (2\text{-}4)$$

$$—R^{f7}(CH_2)_3—SiL_mR_{3-m} \quad (2\text{-}5)$$

Here, the symbols in the formulae (2-1) to (2-5) are as follows.

R$^{f7}$: a C$_{1-20}$ perfluoroalkylene group which may have an etheric oxygen atom
X: a hydrogen atom or a fluorine atom
L: a hydrolysable group
R: a hydrogen atom or a monovalent hydrocarbon group
k: an integer of at least 1
m: an integer of from 1 to 3

<Unit (αβ)>

In the formula (1), a unit (αβ) is the portion represented by [(R$^{f1}$O)$_{x1}$(R$^{f2}$O)$_{x2}$(R$^{f3}$O)$_{x3}$(R$^{f4}$O)$_{x4}$(R$^{f5}$O)$_{x5}$(R$^{f6}$O)$_{x6}$], and a chain ((αβ)$_n$) is the portion represented by [(R$^{f1}$O)$_{x1}$(R$^{f2}$O)$_{x2}$(R$^{f3}$O)$_{x3}$(R$^{f4}$O)$_{x4}$(R$^{f5}$O)$_{x5}$(R$^{f6}$O)$_{x6}$]$_n$. Further, groups (α) are (R$^{f1}$O) and (R$^{f2}$O), and groups (β) are (R$^{f3}$O), (R$^{f4}$O), (R$^{f5}$O) and (R$^{f6}$O). As mentioned above, the bonding order of groups (α) and (β) in the unit (αβ) is not restricted, and the chemical formula of the above unit (αβ) is not meant that the respective groups (α) and the respective groups (β) are bonded in the disclosed order. Further, x1 to x6 are not meant that the respective groups in the unit (αβ) are continuously bonded in the respective numbers, and they are meant to represent the numbers of the respective groups.

n is an integer of at least 2. If the number average molecular weight of the compound (I) is too large, the number of hydrolysable silyl groups present per unit molecular weight decreases and the abrasion resistance lowers, and therefore, the upper limit of n is preferably 45. n is preferably from 4 to 40, particularly preferably from 5 to 35.

x1 is an integer of from 0 to 3. It is preferably 0, since the thermal or chemical stability of (R$^{f1}$O) is inadequate.

x2 is an integer of from 0 to 3. It is preferably an integer of from 1 to 3, particularly preferably 1, since it is thereby possible to impart sufficient abrasion resistance and fingerprint stain removability to the surface-treated layer.

x1+x2 is an integer of from 1 to 3. It is preferably 1 or 2, particularly preferably 1, since it is thereby possible to prevent the number average molecular weight of the compound (1) from becoming too large, while imparting sufficient abrasion resistance and fingerprint stain removability to the surface-treated layer.

x3 is an integer of from 0 to 3. It is preferably an integer of from 1 to 3, particularly preferably 1 or 2, since it is thereby possible to impart sufficient initial water/oil repellency to the surface-treated layer.

x4 is an integer of from 0 to 3. It is preferably an integer of from 1 to 3, more preferably 1 or 2, particularly preferably 1, since it is thereby possible to impart sufficient initial water/oil repellency to the surface-treated layer.

x5 is an integer of from 0 to 3. It is preferably 1, particularly preferably 0, since it is thereby possible to prevent the number average molecular weight of the compound (1) from becoming too large, while imparting sufficient initial water/oil repellency to the surface-treated layer.

x6 is an integer of from 0 to 3. It is preferably 1, particularly preferably 0, since it is thereby possible to prevent the number average molecular weight of the compound (1) from becoming too large, while imparting sufficient initial water/oil repellency to the surface-treated layer.

R$^{f1}$ is a C$_1$ perfluoroalkylene group, i.e. CF$_2$.

R$^{f2}$ is a C$_2$ perfluoroalkylene group. R$^{f2}$ may be linear or branched. It is preferably linear, i.e. CF$_2$CF$_2$, with a view to imparting abrasion resistance and fingerprint stain removability to the surface-treated layer.

R$^{f3}$ is a C$_3$ perfluoroalkylene group. R$^{f3}$ may be linear or branched. It is preferably linear, i.e. CF$_2$CF$_2$CF$_2$, with a view to imparting initial water/oil repellency to the surface-treated layer.

R$^{f4}$ is a C$_4$ perfluoroalkylene group. R$^{f4}$ may be linear or branched. It is preferably linear, i.e. CF$_2$CF$_2$CF$_2$CF$_2$, with a view to imparting initial water/oil repellency to the surface-treated layer.

R$^{f5}$ is a C$_5$ perfluoroalkylene group. R$^{f5}$ may be linear or branched. It is preferably linear, i.e. CF$_2$CF$_2$CF$_2$CF$_2$CF$_2$, with a view to imparting initial water/oil repellency to the surface-treated layer.

R$^{f6}$ is a C$_6$ perfluoroalkylene group. R$^{f6}$ may be linear or branched. It is preferably linear, i.e. CF$_2$CF$_2$CF$_2$CF$_2$CF$_2$CF$_2$, with a view to imparting initial water/oil repellency to the surface-treated layer.

In a unit (αβ), the bonding order of groups (α) and (β) is not limited. That is, the groups (α) and (β) may be randomly arranged, or a group (α) and a group (β) may be alternately arranged. Or, two or more blocks each comprising a plurality of groups, may be linked to one another. It is preferred that the terminal close to A is a group (α) and the terminal close to B is a group (β), since it is thereby possible to further effectively exhibit both the characteristics attributable to the group (α) and the characteristics attributable to the group (β).

The following may be mentioned as specific examples of the unit (αβ).

($CF_2CF_2O$—$CF_2CF_2CF_2O$),
($CF_2CF_2O$—$CF_2CF_2CF_2CF_2O$),
($CF_2CF_2O$—$CF_2CF_2CF_2CF_2CF_2O$),
($CF_2CF_2O$—$CF_2CF_2CF_2CF_2CF_2CF_2O$),
($CF_2CF_2O$—$CF(CF_3)CF_2O$),
($CF_2CF_2OCF_2CF_2O$—$CF_2CF_2CF_2O$),
($CF_2CF_2OCF_2CF_2O$—$CF_2CF_2CF_2CF_2O$),
($CF_2CF_2OCF_2CF_2O$—$CF_2CF_2CF_2CF_2CF_2O$),
($CF_2CF_2OCF_2CF_2O$—$CF_2CF_2CF_2CF_2CF_2CF_2O$),
($CF_2CF_2OCF_2CF_2O$—$CF(CF_3)CF_2O$),
($CF_2CF_2O$—$CF_2CF_2CF_2O$—$CF_2CF_2O$),
($CF_2CF_2O$—$CF_2CF_2CF_2OCF_2CF_2O$),
($CF_2CF_2O$—$CF_2CF_2CF_2OCF_2CF_2CF_2O$),
($CF_2CF_2O$—$CF_2CF_2CF_2OCF_2CF_2CF_2CF_2O$),
($CF_2CF_2O$—$CF_2CF_2CF_2OCF(CF_3)CF_2O$),
($CF_2CF_2O$—$CF_2CF_2CF_2CF_2O$—$CF_2CF_2O$),
($CF_2CF_2O$—$CF_2CF_2CF_2CF_2OCF_2CF_2O$),
($CF_2CF_2O$—$CF_2CF_2CF_2CF_2OCF_2CF_2CF_2O$),
($CF_2CF_2O$—$CF_2CF_2CF_2CF_2OCF(CF_3)CF_2O$),
($CF_2CF_2O$—$CF_2CF_2CF_2CF_2CF_2O$—$CF_2CF_2O$),
($CF_2CF_2O$—$CF_2CF_2CF_2CF_2CF_2OCF_2CF_2O$),
($CF_2CF_2O$—$CF_2CF_2CF_2CF_2CF_2OCF(CF_3)CF_2O$),
($CF_2CF_2O$—$CF_2CF_2CF_2CF_2CF_2CF_2O$—$CF_2CF_2O$),
($CF_2CF_2O$—$CF(CF_3)CF_2O$—$CF_2CF_2O$),
($CF_2CF_2O$—$CF(CF_3)CF_2OCF(CF_3)CF_2O$),
($CF_2CF_2O$—$CF_2CF_2CF_2OCF_2CF_2CF_2O$),
($CF_2CF_2O$—$CF(CF_3)CF_2OCF_2CF_2O$),
($CF_2CF_2OCF_2CF_2OCF_2CF_2O$—$CF_2CF_2CF_2O$),
($CF_2CF_2OCF_2CF_2OCF_2CF_2O$—$CF_2CF_2CF_2CF_2O$),
($CF_2CF_2OCF_2CF_2OCF_2CF_2O$—$CF(CF_3)CF_2O$),
($CF_2CF_2OCF_2CF_2O$—$CF_2CF_2CF_2O$—$CF_2CF_2O$),
($CF_2CF_2OCF_2CF_2O$—$CF(CF_3)CF_2O$—$CF_2CF_2O$),
($CF_2CF_2OCF_2CF_2O$—$CF_2CF_2CF_2OCF_2CF_2O$),
($CF_2CF_2OCF_2CF_2O$—$CF_2CF_2CF_2OCF(CF_3)CF_2O$),
($CF_2CF_2OCF_2CF_2O$—$CF(CF_3)CF_2OCF_2CF_2O$),
($CF_2CF_2OCF_2CF_2O$—$CF(CF_3)CF_2OCF(CF_3)CF_2O$),
($CF_2CF_2OCF_2CF_2OCF_2CF_2O$—$CF_2CF_2O$—$CF_2CF_2O$),
($CF_2CF_2O$—$CF_2CF_2CF_2O$—$CF_2CF_2OCF_2CF_2O$),
($CF_2CF_2O$—$CF_2CF_2CF_2O$—$CF_2CF_2O$—$CF_2CF_2CF_2O$),
($CF_2CF_2O$—$CF_2CF_2CF_2O$—$CF_2CF_2O$—$CF(CF_3)CF_2O$),
($CF_2CF_2O$—$CF(CF_3)CF_2O$—$CF_2CF_2O$—$CF_2CF_2CF_2O$),
($CF_2CF_2O$—$CF(CF_3)CF_2O$—$CF_2CF_2O$—$CF(CF_3)CF_2O$),
($CF_2CF_2O$—$CF_2CF_2CF_2OCF_2CF_2CF_2O$—$CF_2CF_2O$),
($CF_2CF_2O$—$CF_2CF_2CF_2OCF(CF_3)CF_2O$—$CF_2CF_2O$),
($CF_2CF_2O$—$CF(CF_3)CF_2OCF_2CF_2CF_2O$—$CF_2CF_2O$),
($CF_2CF_2O$—$CF(CF_3)CF_2OCF(CF_3)CF_2O$—$CF_2CF_2O$),
($CF_2CF_2O$—$CF_2CF_2CF_2CF_2O$—$CF_2CF_2OCF_2CF_2O$),
($CF_2OCF_2CF_2O$—$CF_2CF_2CF_2O$),
($CF_2OCF_2CF_2O$—$CF_2CF_2CF_2CF_2O$),
($CF_2OCF_2CF_2O$—$CF_2CF_2CF_2CF_2CF_2O$),
($CF_2OCF_2CF_2O$—$CF_2CF_2CF_2CF_2CF_2CF_2O$),
($CF_2OCF_2CF_2O$—$CF(CF_3)CF_2O$),
($CF_2OCF_2CF_2OCF_2CF_2O$—$CF_2CF_2CF_2O$),
($CF_2OCF_2CF_2OCF_2CF_2O$—$CF_2CF_2CF_2CF_2O$),
($CF_2OCF_2CF_2OCF_2CF_2O$—$CF_2CF_2CF_2CF_2CF_2O$),
($CF_2OCF_2CF_2OCF_2CF_2O$—$CF_2CF_2CF_2CF_2CF_2CF_2O$),
($CF_2OCF_2CF_2OCF_2CF_2O$—$CF(CF_3)CF_2O$),
($CF_2OCF_2CF_2O$—$CF_2CF_2CF_2O$—$CF_2CF_2O$),
($CF_2OCF_2CF_2O$—$CF_2CF_2CF_2OCF_2CF_2O$),
($CF_2OCF_2CF_2O$—$CF_2CF_2CF_2OCF_2CF_2CF_2O$),
($CF_2OCF_2CF_2O$—$CF_2CF_2CF_2OCF_2CF_2CF_2CF_2O$),
($CF_2OCF_2CF_2O$—$CF_2CF_2CF_2OCF(CF_3)CF_2O$),
($CF_2OCF_2CF_2O$—$CF_2CF_2CF_2CF_2O$—$CF_2CF_2O$),
($CF_2OCF_2CF_2O$—$CF_2CF_2CF_2CF_2OCF_2CF_2O$),
($CF_2OCF_2CF_2O$—$CF_2CF_2CF_2CF_2OCF_2CF_2CF_2O$),
($CF_2OCF_2CF_2O$—$CF_2CF_2CF_2CF_2OCF(CF_3)CF_2O$),
($CF_2OCF_2CF_2O$—$CF_2CF_2CF_2CF_2CF_2O$—$CF_2CF_2O$),
($CF_2OCF_2CF_2O$—$CF_2CF_2CF_2CF_2CF_2OCF_2CF_2O$),
($CF_2OCF_2CF_2O$—$CF_2CF_2CF_2CF_2CF_2OCF(CF_3)CF_2O$),
($CF_2OCF_2CF_2O$—$CF_2CF_2CF_2CF_2CF_2CF_2O$—$CF_2CF_2O$),
($CF_2OCF_2CF_2O$—$CF(CF_3)CF_2O$—$CF_2CF_2O$),
($CF_2OCF_2CF_2O$—$CF(CF_3)CF_2OCF(CF_3)CF_2O$),
($CF_2OCF_2CF_2O$—$CF(CF_3)OCF_2CF_2CF_2O$),
($CF_2OCF_2CF_2O$—$CF(CF_3)CF_2OCF_2CF_2CF_2O$),
($CF_2OCF_2CF_2OCF_2CF_2OCF_2CF_2O$—$CF_2CF_2CF_2O$),
($CF_2OCF_2CF_2OCF_2CF_2OCF_2CF_2O$—$CF_2CF_2CF_2CF_2O$),
($CF_2OCF_2CF_2OCF_2CF_2OCF_2CF_2O$—$CF(CF_3)CF_2O$),
($CF_2OCF_2CF_2OCF_2CF_2O$—$CF_2CF_2CF_2O$—$CF_2CF_2O$),
($CF_2OCF_2CF_2OCF_2CF_2O$—$CF(CF_3)CF_2O$—$CF_2CF_2O$),
($CF_2OCF_2CF_2OCF_2CF_2O$—$CF_2CF_2CF_2OCF_2CF_2O$),
($CF_2OCF_2CF_2OCF_2CF_2O$—$CF_2CF_2CF_2OCF(CF_3)$$CF_2O$),
($CF_2OCF_2CF_2OCF_2CF_2O$—$CF(CF_3)$$CF_2OCF_2CF_2O$),
($CF_2OCF_2CF_2OCF_2CF_2O$—$CF(CF_3)CF_2OCF(CF_3)$$CF_2O$),
($CF_2OCF_2CF_2OCF_2CF_2O$—$CF_2CF_2CF_2CF_2O$—$CF_2CF_2O$),
($CF_2OCF_2CF_2O$—$CF_2CF_2CF_2O$—$CF_2CF_2OCF_2CF_2O$),
($CF_2OCF_2CF_2O$—$CF_2CF_2CF_2O$—$CF_2CF_2O$—$CF_2CF_2CF_2O$),
($CF_2OCF_2CF_2O$—$CF_2CF_2CF_2O$—$CF_2CF_2O$—$CF(CF_3)$$CF_2O$),
($CF_2OCF_2CF_2O$—$CF(CF_3)CF_2O$—$CF_2CF_2O$—$CF_2CF_2CF_2O$),
($CF_2OCF_2CF_2O$—$CF(CF_3)CF_2O$—$CF_2CF_2O$—$CF(CF_3)$$CF_2O$),
($CF_2OCF_2CF_2O$—$CF_2CF_2CF_2OCF_2CF_2CF_2O$—$CF_2CF_2O$),
($CF_2OCF_2CF_2O$—$CF_2CF_2CF_2OCF(CF_3)CF_2O$—$CF_2CF_2O$),
($CF_2OCF_2CF_2O$—$CF(CF_3)CF_2OCF_2CF_2CF_2O$—$CF_2CF_2O$),
($CF_2OCF_2CF_2O$—$CF(CF_3)CF_2OCF(CF_3)CF_2O$—$CF_2CF_2O$),
($CF_2OCF_2CF_2O$—$CF_2CF_2CF_2CF_2O$—$CF_2CF_2OCF_2CF_2O$),
etc.

As the unit (4), the following are preferred with a view to sufficiently imparting initial water/oil repellency, abrasion resistance and fingerprint stain removability to the surface-treated layer.

($CF_2CF_2O$—$CF_2CF_2CF_2O$),
($CF_2CF_2O$—$CF_2CF_2CF_2CF_2O$),
($CF_2CF_2O$—$CF_2CF_2CF_2OCF_2CF_2CF_2O$),
($CF_2CF_2O$—$CF_2CF(CF_3)OCF_2CF_2CF_2O$),
($CF_2CF_2O$—$CF_2CF_2CF_2CF_2OCF(CF_3)CF_2O$)

<Group A>

A is a $C_{1-6}$ perfluoroalkyl group, a $C_{2-6}$ perfluoroalkyl group having an etheric oxygen atom, or B. From the viewpoint of abrasion resistance, a $C_{1-6}$ perfluoroalkyl group, or a $C_{2-6}$ perfluoroalkyl group having an etheric oxygen atom, is preferred. The perfluoroalkyl group may be linear or branched.

Here, according to the expression of a chemical formula in the present invention, the left-hand side of a chain $((\alpha\beta)_n)$ is a connecting bond of a carbon atom, and therefore, in a case where A is placed on the left-hand side of the chemical formula as shown in the above formula (1), A is expressed as bonded to the chain $((\alpha\beta)_n)$ via an oxygen atom. On the other hand, in a case where A is placed on the right-hand side of the chemical formula, i.e. in the case of an expression wherein A is bonded to a terminal oxygen atom of the chain $((\alpha\beta)_n)$, A is expressed as directly bonded to the terminal oxygen atom of the chain $((\alpha\beta)_n)$ without via an oxygen atom.

The following may be mentioned as specific examples of A.

As a $C_{1-6}$ perfluoroalkyl group,
$CF_3-$,
$CF_3CF_2-$,
$CF_3(CF_2)_2-$,
$CF_3(CF_2)_3-$,
$CF_3(CF_2)_4-$,
$CF_3(CF_2)_5-$,
$CF_3CF(CF_3)-$, etc.

As a $C_{2-6}$ perfluoroalkyl group having an etheric oxygen atom,
$CF_3OCF_2CF_2-$,
$CF_3O(CF_2)_3-$,
$CF_3O(CF_2)_4-$,
$CF_3O(CF_2)_5-$,
$CF_3OCF_2CF_2OCF_2CF_2-$,
$CF_3CF_2OCF_2CF_2-$,
$CF_3CF_2O(CF_2)_3-$,
$CF_3CF_2O(CF_2)_4-$,
$CF_3CF_2OCF_2CF_2OCF_2CF_2-$,
$CF_3(CF_2)_2OCF_2CF_2-$,
$CF_3(CF_2)_2O(CF_2)_3-$,
$CF_3(CF_2)_2OCF(CF_3)CF_2-$,
$CF_3CF(CF_3)OCF_2CF_2-$,
$CF_3CF(CF_3)O(CF_2)_3-$,
$CF_3CF(CF_3)OCF(CF_3)CF_2-$,
$CF_3(CF_2)_3OCF_2CF_2-$, etc.

As A, the following are preferred with a view to sufficiently imparting initial water/oil repellency, abrasion resistance and fingerprint stain removability to the surface-treated layer.
$CF_3-$,
$CF_3CF_2-$,
$CF_3OCF_2CF_2-$,
$CF_3OCF_2CF_2OCF_2CF_2-$,
$CF_3CF_2OCF_2CF_2-$,
$CF_3CF_2O(CF_2)_3-$,
$CF_3CF_2O(CF_2)_4-$,
$CF_3CF_2OCF_2CF_2OCF_2CF_2-$, etc.

<Group B>

The compound (1) has B at one end or both ends of the chain $((\alpha\beta)_n)$. When two B are present in one molecule, they may be the same or different. Here, as mentioned above, according to the expression of a chemical formula in the present invention, in a case where B is placed on the left-hand side of the chemical formula, B is expressed as bonded to the terminal carbon atom of the chain $((\alpha\beta)_n)$ via an oxygen atom, i.e. B—O— is expressed as bonded to the left-hand side of the chain $((\alpha\beta)_n)$.

B is a group represented by one of the formulae (2-1) to (2-5), and the compound (1) has a hydrolysable silyl group represented by $-SiL_mR_{3-m}$ at its terminal. From the viewpoint of handling efficiency in the industrial production, a group represented by the formula (2-3) is particularly preferred.

Hereinafter, a compound (1) wherein B is a group represented by the formula (2-1), will be referred to as a compound (1-1), a compound (1) wherein B is a group represented by the formula (2-2), will be referred to as a compound (1-2), a compound (1) wherein B is a group represented by the formula (2-3), will be referred to as a compound (1-3), a compound (1) wherein B is a group represented by the formula (2-4), will be referred to as a compound (1-4), and a compound (1) wherein B is a group represented by the formula (2-5), will be referred to as a compound (1-5).

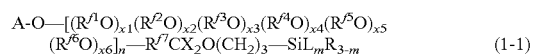  (1-1)

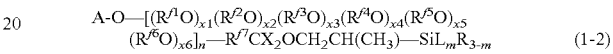  (1-2)

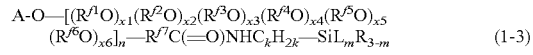  (1-3)

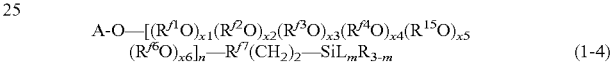  (1-4)

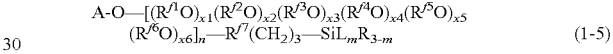  (1-5)

$R^{f7}$ is a $C_{1-20}$ perfluoroalkylene group which may have an etheric oxygen atom. The perfluoroalkylene group may be linear or branched. The following are preferred with a view to sufficiently imparting initial water/oil repellency, abrasion resistance and fingerprint stain removability to the surface-treated layer.
$-CF_2CF_2OCF_2CF_2-$,
$-CF_2CF_2OCF_2CF_2CF_2-$,
$-CF_2CF_2OCF_2CF_2CF_2OCF_2CF_2-$,
$-CF_2CF_2OCF_2CF(CF_3)OCF_2CF_2-$,
$-CF_2CF_2OCF_2CF_2CF_2CF_2OCF(CF_3)-$.

L is a hydrolysable group. The hydrolysable group is a group which becomes a hydroxy group by a hydrolytic reaction. That is, Si-L at the terminal of the compound (I) becomes a silanol group (Si—OH) by a hydrolytic reaction. Silanol groups are further intermolecularly reacted to form a Si—O—Si bond. Further, silanol groups will undergo a dehydration condensation reaction with hydroxy groups (substrate-OH) on the surface of a substrate to form chemical bonds (substrate-O—Si). The compound (1) has a hydrolysable silyl group at its terminal, whereby its adhesion to a substrate is good, and it is a compound excellent in abrasion resistance and capable of imparting water/oil repellency to the surface of the substrate.

L may, for example, be an alkoxy group, a halogen atom, an acyl group, an isocyanate group (—NCO) or the like. The alkoxy group is preferably a $C_{1-4}$ alkoxy group.

L is preferably a $C_{1-4}$ alkoxy group or a halogen atom, whereby an industrial production is easy. The halogen atom is particularly preferably a chlorine atom. L is preferably a $C_{1-4}$ alkoxy group, whereby gas emission during coating is little, and the compound (1) will be excellent in the storage stability. In a case where a long term storage stability of the compound (1) is required, an ethoxy group is particularly preferred, and in a case where it is desired to shorten the reaction time after coating, a methoxy group is particularly preferred.

R is a hydrogen atom or a monovalent hydrocarbon group. The monovalent hydrocarbon group may, for example, be an alkyl group, a cycloalkyl group, an alkenyl group, an allyl group or the like.

R is preferably a monovalent hydrocarbon group, particularly preferably a monovalent saturated hydrocarbon group. The number of carbon atoms in the monovalent saturated hydrocarbon group is preferably from 1 to 6, more preferably from 1 to 3, particularly preferably 1 or 2.

From such a viewpoint that the synthesis is easy, R is preferably a $C_{1-6}$ alkyl group, more preferably a $C_{1-3}$ alkyl group, particularly preferably a $C_{1-2}$ alkyl group.

k is an integer of at least 1, preferably an integer of from 2 to 6, particularly preferably 3. In a case where k is at least 3, $C_kH_{2k}$ may be linear or branched, but is preferably linear.

m is an integer of from 1 to 3, preferably 2 or 3, particularly preferably 3. By the presence of a plurality of L in one molecule, the bonding to the surface of a substrate will be further strengthened.

When m is at least 2, a plurality of L present in one molecule may be the same or different from one another. They are preferably the same one another from the viewpoint of availability of raw material or production efficiency.

The hydrolysable silyl group ($—SiL_mR_{3-m}$) is preferably $—Si(OCH_3)_3$, $—SiCH_3(OCH_3)_2$, $—Si(OCH_2CH_3)_3$, $—SiCl_3$, $—Si(OCOCH_3)_3$, or $—Si(NCO)_3$. From the viewpoint of handling efficiency in the industrial production, $—Si(OCH_3)_3$ is particularly preferred.

Preferred Embodiments

As the compound (1), preferred is a compound having the above-mentioned preferred A and the above-mentioned preferred unit (αβ) combined, and particularly preferred are compounds represented by the following formulae (1-1Ha), (1-1Fa), (1-3a), (1-4a) and (1-5a). In the formula number, H means that X in the formula (1-1) is a hydrogen atom, and F means that X in the formula (1-1) is a fluorine atom. The compounds (1-1Ha), (1-1Fa), (1-3a), (1-4a) and (1-5a) are easy to industrially produce and easy to handle, and can sufficiently impart initial water/oil repellency, abrasion resistance and fingerprint stain removability to the surface-treated layer.

  (1-1Ha),

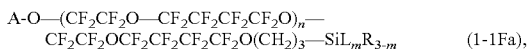  (1-1Fa),

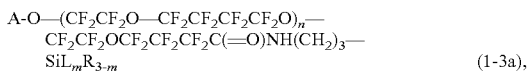  (1-3a),

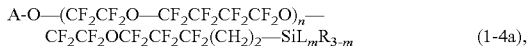  (1-4a),

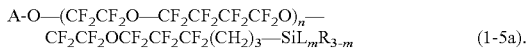  (1-5a).

Here, A is $CF_3—$, $CF_3CF_2—$, $CF_3CF_2OCF_2CF_2CF_2—$, $CF_3OCF_2CF_2—$, $CF_3OCF_2CF_2OCF_2CF_2—$ or $CF_3CF_2OCF_2CF_2OCF_2CF_2—$.

[Method for Producing Fluorinated Ether Compound]

A compound (I) wherein B is a group represented by the formula (2-1) or (2-2), can be produced by a method of introducing a hydrolysable silyl group at a terminal via a step of hydrosilylating a precursor (3) represented by the following formula (3).

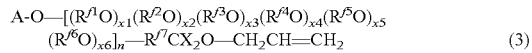  (3)

When the compound (1) is produced via a step of hydrosilylating the precursor (3), a compound (1-1) wherein B is a group represented by the formula (2-1) is obtainable, and at the same time, a compound (1-2) wherein B is a group represented by the formula (2-2) is obtainable as a byproduct. For example, by subjecting the precursor (3) and $HSiL_mR_{3-m}$ (wherein L and R are the same types of the atom or group as in the formula (1), and m is the same numerical value as in the formula (1)) to a hydrosilylation reaction, it is possible to obtain the compounds (1-1) and (1-2). It is preferred to carry out the hydrosilylation reaction by means of a transition metal catalyst such as platinum (Pt) or a radical generating agent such as an organic peroxide.

A compound (1) wherein B is a group represented by the formula (2-3), can be produced by a method of introducing a hydrolysable silyl group at a terminal via a step of reacting a precursor (4) represented by the following formula (4) and an aminoalkyl silane compound. In the formula (4), $R^1$ is an alkyl group, and from the viewpoint of easy synthesis, a $C_{1-3}$ alkyl group is preferred.

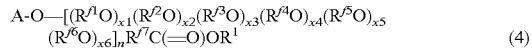  (4)

For example, by an amidation reaction of the precursor (4) and $H_2NC_kH_{2k}SiL_mR_{3-m}$ (wherein L and R are the same types of the atom or group as in the formula (1), and m and k are the same numerical values as in the formula (1)), it is possible to obtain the compound (1-3).

A compound (1) wherein B is a group represented by the formula (2-4), can be produced by a method of introducing a hydrolysable silyl group at a terminal via a step of hydrosilylating a precursor (13) represented by the following formula (13).

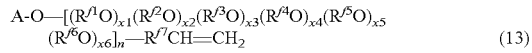  (13)

For example, by subjecting the precursor (13) and $HSiL_mR_{3-m}$ (wherein L and R are the same types of the atom or group as in the formula (1), and m is the same numerical value as in the formula (1)) to a hydrosilylation reaction, it is possible to obtain the compound (1-4).

A compound (1) wherein B is a group represented by the formula (2-5), can be produced by a method of introducing a hydrolysable silyl group at a terminal via a step of hydrosilylating a precursor (14) represented by the following formula (14).

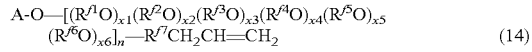  (14)

For example, by subjecting the precursor (14) and $HSiL_mR_{3-m}$ (wherein L and R are the same types of the atom or group as in the formula (1), and m is the same numerical value as in the formula (1)) to a hydrosilylation reaction, it is possible to obtain the compound (1-5).

The precursor (3), (4), (13) or (14) can be produced by a known method depending upon the structure of A-O—$[(R^{f1}O)_{x1}(R^{f2}O)_{x2}(R^{f3}O)_{x3}(R^{f4}O)_{x4}(R^{f5}O)_{x5}(R^{f6}O)_{x6}]_n—$.

The method for producing the precursor (3), (4), (13) or (14) is as follows.

(Method for Producing Precursor (3))

The method for producing the precursor (3) will be described with reference to the case of a precursor (3a) represented by the following formula (3a).

$$\text{A-O—(CF}_2\text{CF}_2\text{O—CF}_2\text{CF}_2\text{CF}_2\text{CF}_2\text{O)}_n\text{—} \\ \text{CF}_2\text{CF}_2\text{OCF}_2\text{CF}_2\text{CF}_2\text{CX}_2\text{O—CH}_2\text{CH=CH}_2 \quad (3a)$$

Hereinafter, the case where X in the formula (3a) is a fluorine atom, will be referred to as a precursor (3Fa), and the case where X is a hydrogen atom, will be referred to as a precursor (3Ha), and examples of the respective production methods will be described.

$$\text{A-O—(CF}_2\text{CF}_2\text{O—CF}_2\text{CF}_2\text{CF}_2\text{CF}_2\text{O)}_n\text{—} \\ \text{CF}_2\text{CF}_2\text{OCF}_2\text{CF}_2\text{CF}_2\text{CF}_2\text{O—CH}_2\text{CH=CH}_2 \quad (3\text{Fa})$$

$$\text{A-O—(CF}_2\text{CF}_2\text{O—CF}_2\text{CF}_2\text{CF}_2\text{CF}_2\text{O)}_n\text{—} \\ \text{CF}_2\text{CF}_2\text{OCF}_2\text{CF}_2\text{CF}_2\text{CH}_2\text{O—CH}_2\text{CH=CH}_2 \quad (3\text{Ha})$$

<Method (i) for Producing Precursor (3Fa)>

A compound (7a) represented by the following formula (7a) is heated in the presence of a metal fluoride catalyst (such as NaF, CsF, KF or AgF) to carry out pyrolysis of the ester, and then allyl bromide (Br—CH$_2$CH=CH$_2$) is reacted to obtain a precursor (3Fa). In the formula (7a), $R^{f8}$ is a $C_{1-11}$ perfluoroalkyl group or a $C_{2-11}$ perfluoroalkyl group having an etheric oxygen atom.

$$\text{A-O—(CF}_2\text{CF}_2\text{O—CF}_2\text{CF}_2\text{CF}_2\text{CF}_2\text{O)}_n\text{—} \\ \text{CF}_2\text{CF}_2\text{OCF}_2\text{CF}_2\text{CF}_2\text{CF}_2\text{O—C(=O)R}^{f8} \quad (7a)$$

<Method (ii) for Producing Precursor (3Fa)>

The precursor (3Fa) can be produced also by the following method.

A compound (8a) represented by the following formula (8a) is reacted with allyl bromide (Br—CH$_2$CH=CH$_2$) in the presence of a metal fluoride catalyst (such as NaF, CsF, KF or AgF) to obtain a precursor (3Fa).

$$\text{A-O—(CF}_2\text{CF}_2\text{O—CF}_2\text{CF}_2\text{CF}_2\text{CF}_2\text{O)}_n\text{—} \\ \text{CF}_2\text{CF}_2\text{OCF}_2\text{CF}_2\text{CF}_2\text{C(=O)F} \quad (8a)$$

<Method for Producing Precursor (3Ha)>

An alcohol (such as methanol, ethanol, 1-propanol or 2-propanol, hereinafter referred to as $R^2$OH wherein $R^2$ is an alkyl group) is reacted to the compound (7a) or (8a) to obtain a compound (6a) represented by the following formula (6a).

$$\text{A-O—(CF}_2\text{CF}_2\text{O—CF}_2\text{CF}_2\text{CF}_2\text{CF}_2\text{O)}_n\text{—} \\ \text{CF}_2\text{CF}_2\text{OCF}_2\text{CF}_2\text{CF}_2\text{C(=O)OR}^2 \quad (6a)$$

Then, the compound (6a) is subjected to hydrogen reduction by means of a reducing agent (such as sodium boron hydride or aluminum lithium hydride) to obtain a compound (5a) represented by the following formula (5a).

$$\text{A-O—(CF}_2\text{CF}_2\text{O—CF}_2\text{CF}_2\text{CF}_2\text{CF}_2\text{O)}_n\text{—} \\ \text{CF}_2\text{CF}_2\text{OCF}_2\text{CF}_2\text{CF}_2\text{CH}_2\text{OH} \quad (5a)$$

The obtained compound (5a) is reacted with allyl bromide (Br—CH$_2$CH=CH$_2$) in the presence of a base (such as sodium hydride, tert-butoxy-potassium, sodium hydroxide or potassium hydroxide) to obtain the precursor (3Ha).

(Method for Producing Precursor (4))

The method for producing the precursor (4) will be described with reference to the case of a precursor (4a) represented by the following formula (4a).

$$\text{A-O—(CF}_2\text{CF}_2\text{O—CF}_2\text{CF}_2\text{CF}_2\text{CF}_2\text{O)}_n\text{—} \\ \text{CF}_2\text{CF}_2\text{OCF}_2\text{CF}_2\text{CF}_2\text{C(=O)OR}^1 \quad (4a)$$

<Method for Producing Precursor (4a)>

The precursor (4a) is the same compound as the compound (6a) except that $R^1$ and $R^2$ are different. As mentioned above, it can be produced by reacting an alcohol to the compound (7a) or (8a).

<Method for Producing Compound (7a)>

The method for producing the compound (7a) will be described with reference to a case where —$R^{f8}$ is —CF(CF$_3$)O(CF$_2$)$_2$CF$_3$.

A compound (11a) represented by the following formula (11a) and an alcohol (such as methanol, ethanol, 1-propanol, 2-propanol, 2,2,2-trifluoroethanol, 2,2,3,3-tetrafluoropropanol, 1,1,1,3,3,3-hexafluoro-2-propanol, 2-methoxyethanol or diethylene glycol monomethyl ether, hereinafter referred to as A$^1$-OH) are reacted in the presence of a base or a quaternary ammonium salt (such as potassium carbonate, sodium carbonate, potassium fluoride, cesium fluoride, sodium hydride, tert-butoxy potassium, sodium hydroxide, potassium hydroxide, tetrabutyl ammonium chloride or tetrabutyl ammonium bromide) to obtain an oligomer compound (10a) represented by the following formula (10a).

$$\text{CF}_2\text{=CFO—CF}_2\text{CF}_2\text{CF}_2\text{CH}_2\text{OH} \quad (11a)$$

$$\text{A}^1\text{-O—(CF}_2\text{CFHO—CF}_2\text{CF}_2\text{CF}_2\text{CH}_2\text{O)}_{n+1}\text{—H} \quad (10a)$$

By controlling the amount of A$^1$-OH to be added to the compound (11a), it is possible to synthesize an oligomer compound (10a) having a desired number average molecular weight. Or, A$^1$-OH may be the compound (11a) itself, and by controlling the reaction time or separation/purification of the product, it is possible to synthesize an oligomer compound (10a) having a desired number average molecular weight.

The synthesis of the compound (11a) and the synthesis of the compound (10a) by its polyaddition reaction can be carried out by known methods disclosed in U.S. Pat. No. 5,134,211.

By an esterification reaction of the compound (10a) and CF$_3$CF$_2$CF$_2$OCF(CF$_3$)COF, a compound (9a) represented by the following formula (9a) is obtained. Such an esterification reaction is not limited to the reaction of the compound (10a) with a perfluoro-acid fluoride as in the above example, and may be a reaction with a fluorinated or non-fluorinated hydrocarbon type acid fluoride, acid chloride, acid bromide or acid anhydride.

$$\text{A}^1\text{-O—(CF}_2\text{CFHO—CF}_2\text{CF}_2\text{CF}_2\text{CH}_2\text{O)}_{n+1}\text{—C(=O)} \\ \text{CF(CF}_3\text{)OCF}_2\text{CF}_2\text{CF}_3 \quad (9a)$$

Further, by means of fluorine gas, hydrogen atoms in the compound (9a) may be substituted by fluorine atoms to obtain the compound (7a). Such a fluorination step can be carried out, for example, in accordance with a method disclosed in WO2000/56694.

(Method for Producing Precursor (13))

The method for producing the precursor (13) will be described with reference to the case of a precursor (13a) represented by the following formula (13a).

$$\text{A-O—(CF}_2\text{CF}_2\text{O—CF}_2\text{CF}_2\text{CF}_2\text{CF}_2\text{O)}_n\text{—} \\ \text{CF}_2\text{CF}_2\text{OCF}_2\text{CF}_2\text{CF}_2\text{CH=CH}_2 \quad (13a)$$

<Method for Producing Precursor (13a)>

The compound (8a) is iodized by means of an iodination agent (such as lithium iodide or iodine/potassium carbonate) to obtain a compound (15a) represented by the following formula (15a).

$$\text{A-O—(CF}_2\text{CF}_2\text{O—CF}_2\text{CF}_2\text{CF}_2\text{CF}_2\text{O)}_n\text{—} \\ \text{CF}_2\text{CF}_2\text{OCF}_2\text{CF}_2\text{CF}_2\text{I} \quad (15a)$$

Then, the compound (15a) is reacted with ethylene in the presence of a radical generating agent to obtain a compound (16a) represented by the following formula (16a).

$$\text{A-O—(CF}_2\text{CF}_2\text{O—CF}_2\text{CF}_2\text{CF}_2\text{CF}_2\text{O)}_n\text{—} \\ \text{CF}_2\text{CF}_2\text{OCF}_2\text{CF}_2\text{CF}_2\text{CH}_2\text{CH}_2\text{I} \quad (16a)$$

The obtained compound (16a) is reacted with allyl bromide (Br—CH$_2$CH=CH$_2$) in the presence of a basic compound (such as sodium hydroxide or potassium hydroxide) for dehydroiodination to obtain the precursor (13a).

(Method for Producing Precursor (14))

The method for producing the precursor (14) will be described with reference to the case of a precursor (14a) represented by the following formula (14a).

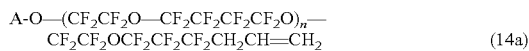
(14a)

<Method for Producing Precursor (14a)>

The compound (15a) is reacted with an allylation agent (such as allyl tributyltin or allyl tris(trimethylsilyl)silane) in the presence of a radical generating agent to obtain a precursor (14a).

[Fluorinated Ether Composition]

The fluorinated ether composition of the present invention (hereinafter referred to as the present composition) is a composition containing at least 95 mass % of the present compound.

The present composition may contain impurities other than the present compound. The impurities other than the present compound mean compounds unavoidable in the production of the present compound. Specifically, they are byproducts formed in the production steps for the present compound and components included in the production steps for the present compound. The present composition does not contain the after-described liquid medium. The content of impurities other than the present compound in the present composition is preferably at most 5 mass %.

The content of the present compound in the present composition is particularly preferably at least 98 mass %. That is, the content of impurities is particularly preferably at most 2 mass %. When the content of the present compound is within such a range, the initial water/oil repellency, abrasion resistance and fingerprint stain removability will be excellent when used for surface treatment of a substrate.

Identification and quantitative determination of byproducts in the present composition are carried out by means of $^1$H-NMR (300.4 MHz) and $^{19}$F-NMR (282.7 MHz). For example, in a case where the desired compounds (1-1) and (1-2) are to be produced via a step of hydrosilylation of the precursor (3), a byproduct will be formed by the hydrosilylation. A case where no spectral peak attributable to such a byproduct (a compound of the formula (1) wherein B is represented by the following formula (2-6)) is detected, is defined that the content of the byproduct is zero. Here, in a case where a spectral peak attributable to the byproduct is observed, the content of the byproduct is obtained by quantitative determination by means of an internal standard.

(2-6)

Likewise, in the case of producing the desired compound (1-4) via a step of hydrosilylation of the precursor (13), a byproduct will be formed by the hydrosilylation. Such a byproduct is a compound (hereinafter referred to as the compound (17)) of the formula (1) wherein B is represented by the following formula (2-7).

(2-7)

Likewise, in the case of producing the desired compound (1-5) via a step of hydrosilylation of the precursor (14), a byproduct will be formed by the hydrosilylation. Such a byproduct is a compound of the formula (1) wherein B is represented by the following formula (2-8).

(2-8)

Further, in the case of producing the desired compounds (1-4) and (1-5), in the reaction of iodizing the compound (8) to obtain the compound (15), a compound (hereinafter referred to as the compound (18)) of the formula (1) wherein B is represented by the following formula (2-9), is likely to be formed as a byproduct.

(2-9)

[Method for Producing Substrate Having Surface-Treated Layer]

(Dry Coating Method)

The present compound and the present composition can be used as they are for a method for producing a substrate having a surface-treated layer, by treating the surface of the substrate by a dry coating method. The present compound and the present composition are suitable to form a surface-treated layer excellent in the adhesion by a dry coating method. The dry coating method may, for example, be a technique such as vacuum deposition, CVD or sputtering. A vacuum deposition method can be suitably used with a view to preventing decomposition of the present compound and in view of simplicity of the apparatus. The vacuum deposition method can be classified into a resistance heating method, an electron beam heating method, a high frequency induction heating method, a reactive deposition method, a molecular beam epitaxy method, a hot wall deposition method, an ion plating method, a cluster ion beam method, etc., and any method can be used. A resistance heating method can be suitably used with a view to preventing decomposition of the present compound and in view of simplicity of the apparatus. The vacuum deposition apparatus is not particularly limited, and a known apparatus may be used.

In a case where a vacuum deposition method is employed, the film deposition conditions vary depending upon the type of the vacuum deposition method to be applied, and in the case of a resistance heating method, the degree of vacuum before deposition is preferably at most $1\times10^{-2}$ Pa, particularly preferably at most $1\times10^{-3}$ Pa. The heating temperature of the deposition source is not particularly limited so long as it is a temperature at which the present compound or the present composition used as the deposition source has a sufficient vapor pressure. It is specifically preferably from 30 to 400° C., particularly preferably from 50 to 300° C. When the heating temperature is at least the lower limit value of the above range, the film deposition rate will be good. When it is at most the upper limit value of the above range, it is possible to impart initial water/oil repellency, abrasion resistance and fingerprint stain removability to the substrate surface without causing decomposition of the present compound. At the time of vacuum deposition, the substrate temperature is preferably within a range of from room temperature (20 to 25° C.) to 200° C. When the substrate temperature is at most 200° C., the film deposition rate will be good. The upper limit value of the substrate temperature is more preferably at most 150° C., particularly preferably at most 100° C.

In a case where the surface of a substrate is treated by a dry coating method using the present compound or the present composition, the surface-treated layer to be formed on the surface of the substrate by the treatment has a film thickness of preferably from 1 to 100 nm, particularly preferably from 1 to 50 nm. When the film thickness of the surface-treated layer is at least the lower limit value of the above range, the effect by the surface treatment is readily sufficiently obtainable. When it is at most the upper limit value of the above range, the utilization efficiency tends to be high. To measure the film thickness, for example, an interference pattern of reflected X-rays is obtained by an X-ray reflectance method using an X-ray diffractometer for thin-film analysis ATX-G (manufactured by Rigaku Corporation), and from the oscillation period of the interference pattern, the film thickness can be calculated.

Particularly, in the vacuum deposition method, the effect to improve the initial water/oil repellency, abrasion resistance and fingerprint stain removability is large, since the content of the present compound in the present composition is large, and the content of impurities is small. This is considered to be such that it is thereby possible to prevent vapor deposition of byproducts having small molecular weights, as impurities, on the surface of a substrate, prior to the present compound, to hinder chemical bonds between the surface of the substrate and the present compound to provide the effect.

(Wet Coating Method)

A substrate having a surface-treated layer can be produced by applying a coating liquid containing the present compound to the surface of a substrate, followed by drying.

As a method for applying the coating liquid, a known technique may suitably be employed.

The application method is preferably a spin coating method, a wipe coating method, a spray coating method, a squeegee coating method, a dip coating method, a die coating method, an ink jet method, a flow coating method, a roll coating method, a casting method, a Langmuir-Blodgett method or a gravure coating method.

The method for drying may be any method so long as it is capable of drying and removing the medium, and a known technique may suitably be employed. The temperature for drying is preferably from 10 to 300° C., particularly preferably from 20 to 200° C.

The surface-treated layer to be formed on the surface of the substrate after the medium is dried and removed has a film thickness of preferably from 1 to 100 nm, particularly preferably from 1 to 50 nm. When the film thickness of the surface-treated layer is at least the lower limit value of the above range, the effect by the surface treatment is readily sufficiently obtainable. When it is at most the upper limit value of the above range, the utilization efficiency tends to be high. Measurement of the film thickness can be carried out in the same manner as the method of measuring the film thickness of the surface-treated layer formed by a dry coating method.

(Post Treatment)

After the surface-treated layer is formed on the substrate surface by the above dry coating method or wet coating method, in order to improve the durability against abrasion of the surface-treated layer, an operation to promote the reaction of the fluorinated ether compound with the substrate may be carried out as the case requires. Such an operation may, for example, be heating, humidification or light irradiation. For example, a substrate having a surface-treated layer formed in an atmosphere containing moisture is heated to promote a reaction such as hydrolysis of the hydrolyzable silyl group into a silanol group, a reaction of the silanol group with e.g. a hydroxy group on the substrate surface, or formation of a siloxane bond by a condensation reaction of silanol groups.

After the surface treatment, a compound in the surface-treated layer which is not chemically bonded to another compound or the substrate, may be removed as the case requires. As a specific method, for example, a method of washing the surface-treated layer with a solvent, or a method of wiping the surface-treated layer with cloth impregnated with a solvent, may be mentioned.

(Coating Liquid)

The coating liquid of the present invention (hereinafter referred to as the present coating liquid) contains the present compound and a medium. The medium is preferably liquid. The present coating liquid is in a liquid form and may be a solution or a dispersion.

The present coating liquid contains the present compound and may contain impurities such as byproducts formed in the production steps for the present compound. Accordingly, the present coating liquid may contain the present composition and a medium.

The concentration of the present compound is preferably from 0.001 to 10 mass %, particularly preferably from 0.1 to 1 mass % in the present coating liquid.

<Medium>

The medium is preferably an organic solvent. The organic solvent may be a fluorinated organic solvent or a non-fluorinated organic solvent, or may contain both solvents.

The fluorinated organic solvent may, for example, be a fluorinated alkane, a fluorinated aromatic compound, a fluoroalkyl ether, a fluorinated alkylamine or a fluoroalcohol.

The fluorinated alkane is preferably a $C_{4-8}$ compound. As commercially available products, for example, $C_6F_{13}H$ (AC-2000, tradename, manufactured by Asahi Glass Company, Limited), $C_6F_{13}C_2H_5$ (AC-6000, tradename, manufactured by Asahi Glass Company, Limited) and $C_2F_5CHFCHFCF_3$ (Vertrel, tradename, manufactured by Du Pont Kabushiki Kaisha) may, for example, be mentioned.

The fluorinated aromatic compound may, for example, be hexafluorobenzene, trifluoromethylbenzene, perfluorotoluene or bis(trifluoromethyl)benzene.

The fluoroalkyl ether is preferably a $C_{4-12}$ compound. As commercially available products, for example, $CF_3CH_2OCF_2CF_2H$ (AE-3000, tradename, manufactured by Asahi Glass Company, Limited), $C_4F_9OCH_3$ (Novec-7100, tradename, manufactured by Sumitomo 3M Limited), $C_4F_9OC_2H_5$ (Novec-7200, tradename, manufactured by Sumitomo 3M Limited) and $C_6F_{13}OCH_3$ (Novec-7300, tradename, manufactured by Sumitomo 3M Limited) may, for example, be mentioned.

The fluorinated alkylamine may, for example, be perfluorotripropylamine or perfluorotributylamine.

The fluoroalcohol may, for example, be 2,2,3,3-tetrafluoropropanol, 2,2,2-trifluoroethanol or hexafluoroisopropanol.

The fluorinated organic solvent is preferably a fluorinated alkane, a fluorinated aromatic compound or a fluoroalkyl ether in view of the solubility of the present compound, and particularly preferred is a fluoroalkyl ether.

The non-fluorinated organic solvent is preferably a compound composed solely of hydrogen atoms and carbon atoms or a compound composed solely of hydrogen atoms, carbon atoms and oxygen atoms, and may, for example, be a hydrocarbon organic solvent, an alcohol organic solvent, a ketone organic solvent, an ether organic solvent or an ester organic solvent.

The hydrocarbon organic solvent is preferably hexane, heptane, cyclohexane or the like.

The alcohol organic solvent is preferably methanol, ethanol, propanol, isopropanol or the like.

The ketone organic solvent is preferably acetone, methyl ethyl ketone, methyl isobutyl ketone or the like.

The ether organic solvent is preferably diethyl ether, tetrahydrofuran, tetraethylene glycol dimethyl ether or the like.

The ester organic solvent is preferably ethyl acetate, butyl acetate or the like.

The non-fluorinated organic solvent is particularly preferably a ketone organic solvent in view of the solubility of the present compound.

The medium is preferably at least one organic solvent selected from the group consisting of the fluorinated alkane, the fluorinated aromatic compound, the fluoroalkyl ether, the compound composed solely of hydrogen atoms and carbon atoms and the compound composed solely of hydrogen atoms, carbon atoms and oxygen atoms. Particularly preferred is a fluorinated organic solvent selected from the fluorinated alkane, the fluorinated aromatic compound and the fluoroalkyl ether.

The medium preferably contains at least one organic solvent selected from the group consisting of the fluorinated alkane, the fluorinated aromatic compound, the fluoroalkyl ether, as fluorinated organic solvents, the compound composed solely of hydrogen atoms, carbon atoms and oxygen atoms, as non-fluorinated solvents, in a total amount of at least 90 mass %, based on the entire medium with a view to increasing the solubility of the present compound.

The present coating liquid contains preferably from 90 to 99.999 mass %, particularly preferably from 99 to 99.99 mass %, of the medium.

The present coating liquid may contain other components in addition to the present compound and the medium, within a range not to impair the effects of the present invention.

Such other components may, for example, be known additives such as an acid catalyst or a basic catalyst, which promotes hydrolysis of the hydrolyzable silyl group and a condensation reaction, etc.

The acid catalyst may, for example, be hydrochloric acid, nitric acid, acetic acid, sulfuric acid, phosphoric acid, sulfonic acid, methanesulfonic acid or p-toluenesulfonic acid.

The basic catalyst may, for example, be sodium hydroxide, potassium hydroxide or ammonia.

In the present coating liquid, the content of other components is preferably at most 10 mass %, particularly preferably at most 1 mass %.

The solid content concentration of the present coating liquid is preferably from 0.001 to 10 mass %, particularly preferably from 0.01 to 1 mass %. The solid content concentration of the coating liquid is a value calculated from the mass of the coating liquid before heating and the mass after the coating liquid is heated by a convection dryer at 120° C. for 4 hours. Further, the concentration of the present composition can be calculated from the solid content concentration and the amounts of charge of the present composition, the medium, etc.

(Substrate)

In the present invention, the substrate to be subjected to surface treatment is not particularly limited so long as it is a substrate to which the water/oil repellency is required to be imparted. The material of the surface of the substrate may, for example, be a metal, a resin, glass, a ceramic or a composite material thereof.

By surface treatment of the substrate using the present compound, the present composition containing it or the present coating liquid to form a surface-treated layer, good initial water/oil repellency is imparted and at the same time, excellent abrasion resistance whereby the water/oil repellency is hardly decreased even by repeated abrasion of the surface, and a performance (fingerprint stain removability) whereby a fingerprint stain on the surface of a substrate can easily be removed, are obtainable. Accordingly, the substrate having a surface-treated layer thus obtained, has good initial water/oil repellency and also has excellent abrasion resistance and fingerprint stain removability, whereby it is useful as a member constituting a touch panel. A touch panel means an input device of an input/display device (touch panel device) comprising a device to input contact location information by contact by e.g. fingers and a display device in combination. The touch panel comprises a substrate, and depending upon the input detection method, a transparent electrically conductive membrane, an electrode, a wiring, an IC, etc. A touch panel having good fingerprint stain removability can be obtained by disposing the substrate so that its surface having a surface-treated layer becomes an input screen of the touch panel.

The material of the substrate for a touch panel has translucency. Here, "has translucency" means that the normal incidence visible light transmittance in accordance with JIS R3106 is at least 25%.

The material of the substrate for a touch panel is preferably glass or a transparent resin. The glass is preferably soda lime glass, alkali aluminosilicate glass, borosilicate glass, alkali-free glass, crystal glass or quartz glass, particularly preferably chemically tempered soda lime glass, chemically tempered alkali aluminosilicate glass or chemically tempered borosilicate glass. The transparent resin substrate is preferably an acrylic resin or polycarbonate.

Further, the substrate in the present invention is also preferably a substrate for a display constituting the outermost surface of a display such as a liquid crystal display, a CRT display, a projection display, a plasma display or an EL display, and by forming a surface-treated layer by surface treatment using the present compound, the present composition or the present coating liquid, good fingerprint stain removability will be obtained.

EXAMPLES

Now, the present invention will be described in further detail with reference to Examples. However, it should be understood that the present invention is by no means restricted to such specific Examples. In the following, "%" means "mass %" unless otherwise specified. Ex. 1 to 9, 11 to 12, 21 to 29 and 31 to 32 are Examples of the present invention, and Ex. 10 and 30 are Comparative Examples.

Ex. 1

Production of Composition (A)

Ex. 1-1

Into a 300 mL three-necked round-bottomed flask, 14.1 g of a sodium borohydride powder was put, and 350 g of AK-225 (tradename, manufactured by Asahi Glass Company, Limited) was added. While cooling and stirring in an ice bath, a solution having 100 g of a compound (12a), 15.8 g of methanol and 22 g of AK-225 mixed, was slowly dropwise added in a nitrogen atmosphere so that the internal temperature would not exceed 10° C. After dropwise addition of the entire amount, a solution having 10 g of methanol and 10 g of AK-225 mixed, was dropwise added. Then, the ice bath was removed, and while raising the temperature slowly to room temperature, stirring was continued. After stirring at room temperature for 12 hours, the reaction mixture was cooled again in an ice bath, and an aqueous hydrochloric acid solution was dropwise added until the liquid became acidic. After termination of the reaction, the reaction mixture was washed once with water and once with a saturated aqueous sodium chloride solution, whereupon an organic phase was recovered. The recovered organic phase was dried over magnesium sulfate, and then, the solid content was filtered off, and the filtrate was concentrated by an evaporator. The recovered concentrated liquid was distilled under reduced pressure to obtain 80.6 g (yield: 88%) of the compound (11a).

$$CF_2=CFO-CF_2CF_2CF_2COOCH_3 \quad (12a)$$

$$CF_2=CFO-CF_2CF_2CF_2CH_2OH \quad (11a)$$

NMR spectrum of compound (11a):
$^1$H-NMR (300.4 MHz, solvent: deuterated chloroform, standard: TMS) δ (ppm): 2.2 (1H), 4.1 (2H)
$^{19}$F-NMR (282.7 MHz, solvent: deuterated chloroform, standard: CFCl$_3$) δ (ppm): −85.6 (2F), −114.0 (1F), −122.2 (1F), −123.3 (2F), −127.4 (2F), −135.2 (1F)

Ex. 1-2-1

Into a 500 mL eggplant flask connected to a reflux condenser, 300 g of the compound (11a) obtained in Ex. 1-1, and 13.5 g of trifluoroethanol (hereinafter referred to as TFEO) were introduced, and 9.34 g of a potassium carbonate powder was added. After stirring at 65° C. for one hour in a nitrogen atmosphere, the temperature was raised to 100° C. over a period of 7 hours, followed by further stirring for 3 hours. By NMR, it was confirmed that the vinyl ether group of the compound (11a) was completely disappeared. Excess potassium carbonate was treated by adding an aqueous hydrochloric acid solution, and water and AK-225 were added to carry out liquid separation treatment. After washing with water three times, the organic phase was recovered and concentrated by an evaporator to obtain 279 g of an oligomer with a high viscosity. It was diluted again with 110 g of AK-225 and developed and fractionated by silica gel column chromatography (developing solvent: AK-225). With respect to each fraction, an average value of the number of units (n+1) was obtained from the integrated value of $^{19}$F-NMR. 47 g of a compound (10a-1i) having fractions with an average value of (n+1) in the following formula (10a-1) being from 7 to 10 put together, and 19 g of a compound (10a-1ii) having fractions with an average value of (n+1) being from 13 to 16 put together, were obtained.

$$CF_3CH_2-O-(CF_2CFHO-CF_2CF_2CF_2CH_2O)_{n+1}-H \quad (10a-1)$$

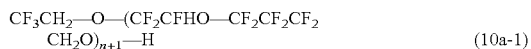

Ex. 1-2-2

Into a 100 mL eggplant flask connected to a reflux condenser, 6.64 g of TFEO was introduced, and 7.32 g of a potassium carbonate powder was added. While stirring at 75° C. in a nitrogen atmosphere, 19.87 g of the compound (11a) obtained in Ex. 1-1 was added, followed by stirring for one hour. Then, the temperature was raised to 120° C., and 113.34 g of the compound (11a) was slowly dropwise added while controlling so that the internal temperature would be at most 130° C. After dropwise addition of the entire amount, stirring was continued for further one hour while maintaining the temperature at 120° C., whereupon heating was terminated, and stirring was continued until the temperature dropped to room temperature. Excess potassium carbonate was treated by adding an aqueous hydrochloric acid solution, and water and AK-225 were added to carry out liquid separation treatment. After washing three times with water, the organic phase was recovered and concentrated by an evaporator to obtain an oligomer with a high viscosity. It was diluted again with 150 g of AK-225 and developed and fractionated by silica gel column chromatography (developing solvent: AK-225). With respect to each fraction, an average value of the number of units (n+1) was obtained from the integrated value of $^{19}$F-NMR. 48.5 g of a compound (10a-1i) having fractions with an average value of (n+1) in the above formula (10a-1) being from 7 to 10 put together, and 13.2 g of a compound (10a-1ii) having fractions with an average value of (n+1) being from 13 to 16 put together, were obtained.

NMR spectrum of compound (10a-1i):
$^1$H-NMR (300.4 MHz, solvent: deuterated acetone, standard: TMS) δ (ppm): 4.1 (2H), 4.8 (16H), 6.7~6.9 (8H)
$^{19}$F-NMR (282.7 MHz, solvent: deuterated acetone, standard: CFCl$_3$) δ (ppm): −74.2 (3F), −84.3~−85.1 (16F), −89.4~−90.5 (16F), −120.2 (14F), −122.0 (2F), −126.6 (14F), −127.0 (2F), −145.1 (8F)
Average value of the number of units (n+1): 8

NMR spectrum of compound (10a-1ii):
$^1$H-NMR (300.4 MHz, solvent: deuterated acetone, standard: TMS) δ (ppm): 4.1 (2H), 4.8 (28H), 6.7~6.9 (14H)
$^{19}$F-NMR (282.7 MHz, solvent: deuterated acetone, standard: CFCl$_3$) δ (ppm): −74.2 (3F), −84.3~−85.1 (28F), −89.4~−90.5 (28F), −120.2 (26F), −122.0 (2F), −126.6 (26F), −127.0 (2F), −145.1 (14F)
Average value of the number of units (n+1): 14

Ex. 1-3

Into a 300 mL eggplant flask connected to a reflux condenser, 113.33 g of the compound (10a-1i) obtained in Ex. 1-2, 5.0 g of a sodium fluoride powder and 150 g of AK-225 were introduced, and 84.75 g of CF$_3$CF$_2$CF$_2$OCF (CF$_3$)COF was added. After stirring at 50° C. for 13 hours in a nitrogen atmosphere, stirring was continued at 70° C. for 3 hours. After removing the sodium fluoride powder by pressure filtration, excess CF$_3$CF$_2$CF$_2$OCF(CF$_3$)COF and AK-225 were distilled off under reduced pressure. By silica gel column chromatography (developing solvent: AK-225), highly polar impurities were removed to obtain 100.67 g (yield: 80%) of a compound (9a-1i) of the following formula (9a-1) wherein the average value of the number of units (n+1) is 8.

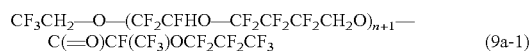

NMR spectrum of compound (9a-1i):
$^1$H-NMR (300.4 MHz, solvent: deuterated chloroform, standard: TMS) δ (ppm): 4.4 (16H), 4.9 (2H), 6.0-6.2 (8H)
$^{19}$F-NMR (282.7 MHz, solvent: deuterated chloroform, standard: CFCl$_3$) δ (ppm): −75.2 (3F), −80.0 (1F), −81.9 (3F), −82.7 (3F), −84.7~−85.0 (16F), −86.0 (1F), −90.5~−93.0 (16F), −121.1 (2F), −121.5 (14F), −128.0 (16F), −130.3 (2F), −132.5 (1F), −145.3 (8F)
Average value of the number of units (n+1): 8

Ex. 1-4

An autoclave (made of nickel, internal capacity: 1 L) was provided, and at a gas discharge outlet of the autoclave, a condenser held at 0° C., a NaF pellets-packed layer and a condenser held at −10° C. were set in series. Further, a liquid-returning line to return a liquid condensed from the condenser held at −10° C. to the autoclave, was set.

Into the autoclave, 750 g of R-113 (CF$_2$ClCFCl$_2$) was put and stirred while maintaining the temperature at 25° C. After blowing nitrogen gas at 25° C. for one hour into the autoclave, fluorine gas diluted to 20 vol % with nitrogen gas (hereinafter referred to as the 20% fluorine gas), was blown into it at 25° C. for one hour at a flow rate of 3.2 L/hr. While blowing the 20% fluorine gas at the same flow rate, a solution having 130 g of the compound (9a-1i) obtained in Ex. 1-3 dissolved in 448 g of R-113, was injected into the autoclave over a period of 22 hours.

Then, while blowing the 20% fluorine gas at the same flow rate, the internal pressure of the autoclave was raised to 0.15 MPa (gauge pressure). Into the autoclave, 8 mL of a benzene solution containing 0.015 g/mL of benzene in R-113, was injected while heating to from 25° C. to 40° C., whereupon the benzene solution injection inlet of the autoclave was closed. After stirring for 20 minutes, 4 mL of the benzene solution was injected again while maintaining the temperature at 40° C., whereupon the injection inlet was closed. The same operation was further repeated 7 times. The total injected amount of benzene was 0.6 g.

Further, stirring was continued for one hour while blowing the 20% fluorine gas at the same flow rate. Then, the internal pressure of the autoclave was adjusted to the atmospheric pressure, and nitrogen gas was injected for one hour. The content in the autoclave was concentrated by an evaporator to obtain 152.1 g (yield: 99%) of a compound (7a-1i) of the following formula (7a-1) wherein the average value of the number of units (n) is 7.

$$CF_3CF_2-O-(CF_2CF_2O-CF_2CF_2CF_2CF_2O)_n-\\CF_2CF_2OCF_2CF_2CF_2CF_2O-C(=O)CF(CF_3)\\OCF_2CF_2CF_3 \quad (7a\text{-}1)$$

NMR spectrum of compound (7a-1i):
$^{19}$F-NMR (282.7 MHz, solvent: deuterated chloroform, standard:CFCl$_3$) δ (ppm): −80.0 (1F), −82.0~−82.5 (6F), −84.0 (30F), −86.7~−87.8 (6F), −89.2 (34F), −126.5 (32F), −130.4 (2F), −132.4 (1F)

Average value of the number of units (n): 7

Ex. 1-5

Into a 500 mL round-bottomed eggplant flask made of a tetrafluoroethylene/perfluoro(alkoxy vinyl ether) copolymer (hereinafter referred to as PFA), 120 g of the compound (7a-1i) obtained in Ex. 1-4 and 240 g of AK-225 were put. While cooling and stirring in an ice bath, 6.1 g of methanol was slowly dropwise added from a dropping funnel in a nitrogen atmosphere. Stirring was continued for 12 hours while bubbling with nitrogen. The reaction mixture was concentrated by an evaporator to obtain 108.5 g (yield: 100%) of a precursor (4a-1i) of the following formula (4a-1) wherein the average value of the number of units (n) is 7.

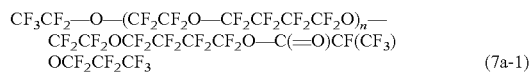

$$CF_3CF_2-O-(CF_2CF_2O-CF_2CF_2CF_2CF_2O)_n-\\CF_2CF_2OCF_2CF_2CF_2C(=O)OCH_3 \quad (4a\text{-}1)$$

NMR spectrum of precursor (4a-1i):
$^1$H-NMR (300.4 MHz, solvent: deuterated chloroform, standard: TMS) δ (ppm): 3.9 (3H)
$^{19}$F-NMR (282.7 MHz, solvent: deuterated chloroform, standard: CFCl$_3$) δ (ppm): −84.0 (30F), −88.2 (3F), −89.2 (34F), −119.8 (2F), −126.5 (30F)

Average value of the number of units (n): 7

Ex. 1-6

Into a 300 mL eggplant flask, 92.5 g of the precursor (4a-1i) obtained in Ex. 1-5 and 6.51 g of H$_2$NCH$_2$CH$_2$CH$_2$Si(OCH$_3$)$_3$ were put and stirred for 12 hours. From NMR, it was confirmed that 98% of the precursor (4a-1i) was converted to a compound (1-3a-1i). Further, all of H$_2$NCH$_2$CH$_2$CH$_2$Si(OCH$_3$)$_3$ was reacted, and methanol was formed as a byproduct. Thus, a composition (A) containing 97% of the compound (1-3a-1i) of the following formula (1-3a-1) wherein the average value of the number of units (n) is 7, was obtained. The number average molecular weight of the compound (1-3a-1i) was 2,900. The results are shown in Table 1.

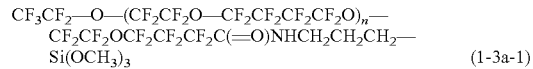

$$CF_3CF_2-O-(CF_2CF_2O-CF_2CF_2CF_2CF_2O)_n-\\CF_2CF_2OCF_2CF_2CF_2C(=O)NHCH_2CH_2CH_2-\\Si(OCH_3)_3 \quad (1\text{-}3a\text{-}1)$$

NMR spectrum of compound (1-3a-1i):
$^1$H-NMR (300.4 MHz, solvent: deuterated chloroform, standard: TMS) δ (ppm): 0.6 (2H), 1.6 (2H), 2.8 (1H), 3.3 (2H), 3.5 (9H)
$^{19}$F-NMR (282.7 MHz, solvent: deuterated chloroform, standard: CFCl$_3$) δ (ppm): −84.1 (30F), −87.9 (3F), −89.3 (34F), −120.8 (2F), −126.6 (28F), −127.2 (2F)

Average value of the number of units (n): 7

Ex. 2

Production of Composition (B)

Ex. 2-1

Into a 200 mL eggplant flask connected to a reflux condenser, 114.72 g of the compound (10a-1ii) obtained in Ex. 1-2-1, 8.1 g of a sodium fluoride powder and 101.72 g of AK-225 were introduced, and 95.18 g of CF$_3$CF$_2$CF$_2$OCF(CF$_3$)COF was added. After stirring at 50° C. for 12 hours in a nitrogen atmosphere, stirring was continued at room temperature overnight. After removing the sodium fluoride powder by pressure filtration, excess CF$_3$CF$_2$CF$_2$OCF(CF$_3$)COF and AK-225 were distilled off under reduced pressure. By silica gel column chromatography (developing solvent: AK-225), highly polar impurities were removed to obtain 94.57 g (yield: 77%) of a compound (9a-1ii) of the above formula (9a-1) wherein the average value of the number of units (n+1) is 14.

NMR spectrum of compound (9a-1ii):
$^1$H-NMR (300.4 MHz, solvent: deuterated chloroform, standard: TMS) δ (ppm): 4.4 (28H), 4.9 (2H), 6.0-6.2 (14H)
$^{19}$F-NMR (282.7 MHz, solvent: deuterated chloroform, standard: CFCl$_3$) δ (ppm): −75.2 (3F), −80.0 (1F), −81.9 (3F), −82.7 (3F), −84.7~−85.0 (28F), −86.0 (1F), −90.5~−93.0 (28F), −121.1 (2F), −121.5 (26F), −128.0 (28F), −130.3 (2F), −132.5 (1F), −145.3 (14F)

Average value of the number of units (n+1): 14

Ex. 2-2

An autoclave (made of nickel, internal capacity: 3 L) was provided, and at a gas discharge outlet of the autoclave, a condenser held at 0° C., a NaF pellets-packed layer and a condenser held at −10° C. were set in series. Further, a liquid-returning line to return a liquid condensed from the condenser held at −10° C. to the autoclave, was set.

Into the autoclave, 2,350 g of R-113 was put and stirred while maintaining the temperature at 25° C. After blowing nitrogen gas at 25° C. for one hour into the autoclave, the 20% fluorine gas was blown into it at 25° C. for one hour at a flow rate of 4.2 L/hr. Then, while blowing the 20% fluorine gas at the same flow rate, a solution having 213 g of the compound (9a-1ii) obtained in Ex. 2-1 dissolved in 732 g of R-113, was injected into the autoclave over a period of 29 hours.

Then, while blowing the 20% fluorine gas at the same flow rate, the internal pressure of the autoclave was raised to 0.15 MPa (gauge pressure). Into the autoclave, 4 mL of a benzene solution containing 0.009 g/mL of benzene in R-113, was injected while heating to from 25° C. to 40° C., whereupon the benzene solution injection inlet of the autoclave was closed. After stirring for 20 minutes, 5 mL of the benzene solution was injected again while maintaining the temperature at 40° C., whereupon the injection inlet was closed. The same operation was further repeated 7 times. The total injected amount of benzene was 0.4 g.

Further, stirring was continued for one hour while blowing the 20% fluorine gas at the same flow rate. Then, the internal pressure of the autoclave was adjusted to the atmospheric pressure, and nitrogen gas was injected for one hour. The content in the autoclave was concentrated by an evaporator to obtain 250.1 g (yield: 99%) of a compound (7a-1ii) of the above formula (7a-1) wherein the average value of the number of units (n) is 13.

NMR spectrum of compound (7a-1ii):
$^{19}$F-NMR (282.7 MHz, solvent: deuterated chloroform, standard: CFCl$_3$) δ (ppm): −80.3 (1F), −82.0~−82.5 (6F), −84.2 (54F), −86.9~−88.0 (6F), −89.4 (58F), 126.6 (56F), −130.4 (2F), −132.4 (1F)

Average value of the number of units (n): 13

Ex. 2-3

Into a 500 mL round-bottomed eggplant flask made of PFA, 110 g of the compound (7a-1ii) obtained in Ex. 2-2 and 220 g of AK-225 were put. While cooling and stirring in an ice bath, 3.5 g of methanol was slowly dropwise added from a dropping funnel in a nitrogen atmosphere. Stirring was continued for 12 hours while bubbling with nitrogen. The reaction mixture was concentrated by an evaporator to obtain 103 g (yield: 100%) of a precursor (4a-1ii) of the above formula (4a-1) wherein the average value of the number of units (n) is 13.

NMR spectrum of precursor (4a-1ii):
$^{1}$H-NMR (300.4 MHz, solvent: deuterated chloroform, standard: TMS) δ (ppm): 3.9 (3H)
$^{19}$F-NMR (282.7 MHz, solvent: deuterated chloroform, standard: CFCl$_3$) δ (ppm): −84.0 (54F), −88.2 (3F), −89.2 (58F), −119.8 (2F), −126.5 (54F)

Average value of the number of units (n): 13

Ex. 2-4

Into a 300 mL eggplant flask, 100.5 g of the precursor (4a-1ii) obtained in Ex. 2-3 and 4.38 g of H$_2$NCH$_2$CH$_2$CH$_2$Si(OCH$_3$)$_3$ were put and stirred for 12 hours. From NMR, it was confirmed that 98% of the precursor (4a-1ii) was converted to a compound (1-3a-1ii). Further, all of H$_2$NCH$_2$CH$_2$CH$_2$Si(OCH$_3$)$_3$ was reacted, and methanol was formed as a byproduct. Thus, a composition (B) containing 97% of the compound (1-3a-1ii) of the above formula (I-3a-1) wherein the average value of the number of units (n) is 13, was obtained. The number average molecular weight of the compound (1-3a-1ii) was 4,900. The results are shown in Table 1.

NMR spectrum of compound (1-3a-1ii):
$^{1}$H-NMR (300.4 MHz, solvent: deuterated chloroform, standard: TMS) δ (ppm): 0.6 (2H), 1.6 (2H), 2.8 (1H), 3.3 (2H), 3.5 (9H)
$^{19}$F-NMR (282.7 MHz, solvent: deuterated chloroform, standard: CFCl$_3$) δ (ppm): −84.1 (54F), −87.9 (3F), −89.3 (58F), −120.8 (2F), −126.6 (52F), −127.2 (2F)

Average value of the number of units (n): 13

Ex. 3

Production of Mixture (C)

Ex. 3-1

Into a 500 mL three-necked eggplant flask, 0.92 g of lithium chloride was dissolved in 91.6 g of ethanol. 120.0 g of the precursor (4a-1i) obtained in Ex. 1-5, i.e. the compound (6a-1i), was added thereto, and while cooling in an ice bath, a solution having 3.75 g of sodium borohydride dissolved in 112.4 g of ethanol, was slowly dropwise added. Thereafter, the ice bath was removed, and stirring was continued while raising the temperature slowly to room temperature. After stirring at room temperature for 12 hours, an aqueous hydrochloric acid solution was dropwise added until the liquid became acidic. 100 mL of AK-225 was added, and after washing once with water and once with a saturated sodium chloride aqueous solution, the organic phase was recovered. The recovered organic phase was concentrated by an evaporator to obtain 119.0 g (yield: 100%) of a compound (5a-1i) of the following formula (5a-1) wherein the average value of the number of units (n) is 7.

(5a-1)

NMR spectrum of compound (5a-1i):
$^{1}$H-NMR (300.4 MHz, solvent: deuterated chloroform, standard: TMS) δ (ppm): 1.8 (1H), 4.0 (2H)
$^{19}$F-NMR (282.7 MHz, solvent: deuterated chloroform, standard: CFCl$_3$) δ (ppm): −84.1 (30F), −87.7 (3F), −89.3 (34F), −123.7 (2F), −126.6 (28F), −127.8 (2F)

Average value of the number of units (n): 7

Ex. 3-2

Into a 500 mL three-necked eggplant flask, 2.26 g of sodium hydride was suspended in 22.6 g of tetrahydrofuran (hereinafter referred to as THF). A solution having 118.5 g of the compound (5a-1i) obtained in Ex. 3-1 diluted with 212.4 g of AC-2000 (tradename, manufactured by Asahi Glass Company, Limited), was dropwise added thereto, and further, 15.7 g of allyl bromide was dropwise added. The mixture was adjusted to 70° C. in an oil bath and stirred for 5 hours. The obtained reaction crude liquid was washed once with water and once with a saturated sodium chloride aqueous solution, and the organic phase was recovered. The recovered organic phase was passed through a silica gel column, and the recovered solution was concentrated by an evaporator and washed three times with hexane to obtain 99.9 g (yield: 83%) of a precursor (3Ha-1i) of the following formula (3Ha-1) wherein the average value of the number of units (n) is 7.

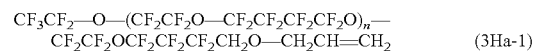

(3Ha-1)

NMR spectrum of precursor (3Ha-1i):
$^{1}$H-NMR (300.4 MHz, solvent: deuterated chloroform, standard: TMS) δ (ppm): 3.8 (2H), 4.1 (2H), 5.2 (2H), 5.9 (2H)
$^{19}$F-NMR (282.7 MHz, solvent: deuterated chloroform, standard: CFCl$_3$) δ (ppm): −84.1 (30F), −87.7 (3F), −89.3 (34F), −120.5 (2F), −126.6 (28F), −127.6 (2F)

Average value of the number of units (n): 7

Ex. 3-3

Into a 100 mL closed type pressure resistant container made of polytetrafluoroethylene (hereinafter referred to as PTFE), 49.0 g of the precursor (3Ha-11) obtained in Ex. 3-2, 0.26 g of di-tert-butyl peroxide, 23.7 g of trichlorosilane and 24.5 g of HFE-7300 (tradename, manufactured by 3M) were put and stirred at 120° C. for 8 hours. After distilling off unreacted substances, solvent, etc. by concentration under reduced pressure, the reaction mixture was put into a flask equipped with a dropping funnel, and 50 g of HFE-7300 was put, followed by stirring at room temperature. 15.0 g of a mixed solution of trimethyl orthoformate and methanol (trimethyl orthoformate:methanol=25:1 [mol:mol]) was dropwise added and reacted at 60° C. for 3 hours. After completion of the reaction, the solvent, etc. were distilled off under reduced pressure, and to the residue, 0.05 g of activated carbon was added, followed by stirring for one hour, and then, filtration was carried out by means of a membrane filter with a pore diameter of 0.5 μm to obtain 49.5 g (yield: 97%) of a mixture (C) of a compound (1-1Ha-1i) of the following formula (I-1Ha-1) wherein the average value of the number of units (n) is 7 and a compound (1-2Ha-1i) of the following formula (I-2Ha-1) wherein the average value of the number of units (n) is 7. The molar ratio of the compound (1-1Ha-1i) to the compound (1-2Ha-1i) was 93:7 from NMR. The number average molecular weight of the mixture (C) was 2,900. The results are shown in Table 1.

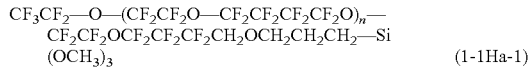

(1-1Ha-1)

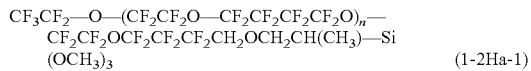

(1-2Ha-1)

NMR spectrum of compound (1-1Ha-1i):
$^1$H-NMR (300.4 MHz, solvent: deuterated chloroform, standard: TMS) δ (ppm): 0.7 (2H), 1.7 (2H), 3.6 (11H), 3.8 (2H)
$^{19}$F-NMR (282.7 MHz, solvent: deuterated chloroform, standard: CFCl$_3$) δ (ppm): −84.1 (30F), −87.7 (3F), −89.3 (34F), −120.8 (2F), −126.6 (28F), −127.6 (2F)

NMR spectrum of compound (1-2Ha-1i):
$^1$H-NMR (300.4 MHz, solvent: deuterated chloroform, standard: TMS) δ (ppm): 1.1 (3H), 1.8 (1H), 3.6 (11H), 3.8 (2H)
$^{19}$F-NMR (282.7 MHz, solvent: deuterated chloroform, standard: CFCl$_3$) δ (ppm): −84.1 (30F), −87.7 (3F), −89.3 (34F), −120.8 (2F), −126.6 (28F), −127.6 (2F)
Average value of the number of units (n): 7

Ex. 4

Production of Mixture (D)

Ex. 4-1

Into a 500 mL three-necked eggplant flask, 0.57 g of lithium chloride was dissolved in 57.0 g of ethanol. 128.0 g of the precursor (4a-1ii) obtained in Ex. 2-3, i.e. the compound (6a-1ii), was added thereto, and while cooling in an ice bath, a solution having 2.33 g of sodium borohydride dissolved in 69.9 g of ethanol, was slowly dropwise added. Thereafter, the ice bath was removed, and stirring was continued while raising the temperature slowly to room temperature. After stirring at room temperature for 12 hours, an aqueous hydrochloric acid solution was dropwise added until the liquid became acidic. 100 mL of AK-225 was added, and after washing once with water and once with a saturated sodium chloride aqueous solution, the organic phase was recovered. The recovered organic phase was concentrated by an evaporator to obtain 127.3 g (yield: 100%) of a compound (5a-1ii) of the above formula (5a-1) wherein the average value of the number of units (n) is 13.

NMR spectrum of compound (5a-1ii):
$^1$H-NMR (300.4 MHz, solvent: deuterated chloroform, standard: TMS) δ (ppm): 2.1 (1H), 4.0 (2H)
$^{19}$F-NMR (282.7 MHz, solvent: deuterated chloroform, standard: CFCl$_3$) δ (ppm): −84.1 (54F), −87.7 (3F), −89.3 (58F), −123.7 (2F), −126.6 (52F), −127.8 (2F)
Average value of the number of units (n): 13

Ex. 4-2

Into a 500 mL three-necked eggplant flask, 1.40 g of sodium hydride was suspended in 14.0 g of THF. A solution having 127.0 g of the compound (5a-1ii) obtained in Ex. 4-1 diluted with 211.5 g of AC-2000 was dropwise added thereto, and further, 9.71 g of allyl bromide was dropwise added. The mixture was adjusted to 70° C. in an oil bath and stirred for 5 hours. The obtained reaction crude liquid was washed once with water and once with a saturated sodium chloride aqueous solution, and the organic phase was recovered. The recovered organic phase was passed through a silica gel column, and the recovered solution was concentrated by an evaporator and washed three times with hexane to obtain 103.4 g (yield: 81%) of a precursor (3Ha-1ii) of the above formula (3Ha-1) wherein the average value of the number of units (n) is 13.

NMR spectrum of precursor (3Ha-1ii):
$^1$H-NMR (300.4 MHz, solvent: deuterated chloroform, standard: TMS) δ (ppm): 3.8 (2H), 4.1 (2H), 5.2 (2H), 5.9 (2H)
$^{19}$F-NMR (282.7 MHz, solvent: deuterated chloroform, standard: CFCl$_3$) δ (ppm): −84.1 (54F), −87.7 (3F), −89.3 (58F), −120.5 (2F), −126.6 (52F), −127.6 (2F)
Average value of the number of units (n): 13

Ex. 4-3

Into a 100 mL closed type pressure resistant container made of PTFE, 51.0 g of the precursor (3Ha-1ii) obtained in Ex. 4-2, 0.16 g of di-tert-butyl peroxide, 12.6 g of trichlorosilane and 30.6 g of HFE-7300 were put and stirred at 120° C. for 8 hours. After distilling off unreacted substances, solvent, etc. by concentration under reduced pressure, the reaction mixture was put into a flask equipped with a dropping funnel, and 50 g of HFE-7300 was put, followed by stirring at room temperature. 9.1 g of a mixed solution of trimethyl orthoformate and methanol (trimethyl orthoformate:methanol=25:1 [mol:mol]) was dropwise added and reacted at 60° C. for 3 hours. After completion of the reaction, the solvent, etc. were distilled off under reduced pressure, and to the residue, 0.05 g of activated carbon was added, followed by stirring for one hour, and then, filtration was carried out by means of a membrane filter with a pore diameter of 0.5 μm to obtain 51.1 g (yield: 98%) of a mixture (D) of a compound (1-1Ha-1ii) of the above formula (I-1Ha-1) wherein the average value of the number of units (n) is 13 and a compound (1-2Ha-1ii) of the above formula (I-2Ha-1) wherein the average value of the number of units (n) is 13.

The molar ratio of the compound (1-1Ha-1ii) to the compound (1-2Ha-1ii) was 93:7 from NMR. The number average molecular weight of the mixture (D) was 4,900. The results are shown in Table 1.

NMR spectrum of compound (1-1Ha-1ii):
$^1$H-NMR (300.4 MHz, solvent: deuterated chloroform, standard: TMS) δ (ppm): 0.7 (2H), 1.7 (2H), 3.6 (11H), 3.8 (2H)
$^{19}$F-NMR (282.7 MHz, solvent: deuterated chloroform, standard: CFCl$_3$) δ (ppm): −84.1 (54F), −87.7 (3F), −89.3 (58F), −120.8 (2F), −126.6 (52F), −127.6 (2F)

NMR spectrum of compound (1-2Ha-1ii):
$^1$H-NMR (300.4 MHz, solvent: deuterated chloroform, standard: TMS) δ (ppm): 1.1 (3H), 1.8 (1H), 3.6 (11H), 3.8 (2H)
$^{19}$F-NMR (282.7 MHz, solvent: deuterated chloroform, standard: CFCl$_3$) δ (ppm): −84.1 (54F), −87.7 (3F), −89.3 (58F), −120.8 (2F), −126.6 (52F), −127.6 (2F)

Average value of the number of units (n): 13

Ex. 5

Production of Compound (E)

Ex. 5-1

Into a 50 mL eggplant flask, 10.5 g of the compound (7a-1i) obtained in Ex. 1-4 and 0.32 g of CsF were put and heated to 80° C. to carry out pyrolysis of the ester, and in order to remove low boiling point components as byproducts out of the system, the pressure was reduced to 10 mmHg while maintaining the temperature at 80° C. and maintained for one hour. A part was sampled and analyzed by NMR, whereby formation of a compound (8a-1) was confirmed.

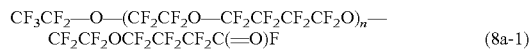
(8a-1)

Ex. 5-2

Then, 8.0 g of tetraglyme and 1.12 g of CsF were added to the eggplant flask, followed by stirring at 50° C. for one hour in a nitrogen atmosphere. While maintaining the temperature at 50° C., 0.80 g of allyl bromide was dropwise added. The temperature was raised to 80° C., and the reaction was carried out for 12 hours in a nitrogen atmosphere. After completion of the reaction, extraction and washing were carried out with HFE-7300 as a fluorinated solvent and water, and after separation into two layers, the organic phase was recovered. To the organic phase, a 5% sodium hydride aqueous solution was added, followed by stirring for 30 minutes, whereupon the organic phase after separation into two layers, was recovered. The solvent in the recovered phase was distilled off under reduced pressure, followed by filtration through a membrane filter with a pore diameter of 0.5 μm to obtain 2.3 g (yield: 24%) of a precursor (3Fa-1).

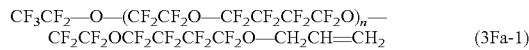
(3Fa-1)

NMR spectrum of precursor (3Fa-1):
$^1$H-NMR (300.4 MHz, solvent: deuterated chloroform, standard: TMS) δ (ppm): 4.5 (2H), 5.3 (2H), 5.9 (2H)
$^{19}$F-NMR (282.7 MHz, solvent: deuterated chloroform, standard: CFCl$_3$) δ (ppm): −84.1 (30F), −86.1 (2F), −87.7 (3F), −89.3 (34F), −126.1 (2F), −126.6 (30F)
Average value of the number of units (n): 7

Ex. 5-3

Into a 25 mL eggplant flask, 2.3 g of the precursor (3Fa-1) obtained in Ex. 5-2, 0.005 g of a platinum/1,3-divinyl-1,1,3,3-tetramethyldisiloxane complex xylene solution (platinum content: 2%) and 0.55 g of trichlorosilane were put and stirred at 60° C. for 4 hours. After distilling off unreacted substances, solvent, etc. by concentration under reduced pressure, the reaction mixture was put into a flask equipped with a dropping funnel, and 5 g of 1,3-bis(trifluoromethyl)benzene was put, followed by stirring at room temperature. 0.75 g of a mixed solution of trimethyl orthoformate and methanol (trimethyl formatted:methanol=25:1 [mol:mol]) was dropwise added, and the reaction was carried out at 60° C. for 3 hours. After completion of the reaction, the solvent, etc. were distilled off under reduced pressure, and to the residue, 0.05 g of activated carbon was added, followed by stirring for one hour, and then filtration was carried out by means of a membrane filter with a pore diameter of 0.5 μm to obtain 2.0 g (yield: 83%) of a compound (1-1Fa-1) (hereinafter referred to also as the compound (E)). The number average molecular weight of the compound (E) was 3,000. The results are shown in Table 1.

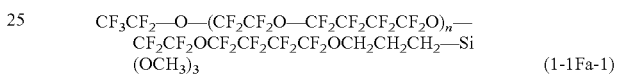
(1-1Fa-1)

NMR spectrum of compound (1-1Fa-1):
$^1$H-NMR (300.4 MHz, solvent: deuterated chloroform, standard: TMS) δ (ppm): 0.7 (2H), 1.8 (2H), 3.6 (9H), 4.0 (2H)
$^{19}$F-NMR (282.7 MHz, solvent: deuterated chloroform, standard: CFCl$_3$) δ (ppm): −84.1 (30F), −86.2 (2F), −87.7 (3F), −89.3 (34F), −126.1 (2F), −126.5 (30F)
Average value of the number of units (n): 7

Ex. 6

Production of Composition (F)

Ex. 6-1

Into a 50 mL eggplant flask connected to a reflux condenser, 5.01 g of the compound (11a) obtained in Ex. 1-1, and 5.06 g of methanol were introduced, and 0.54 g of pellets of potassium hydroxide was added. After stirring at 25° C. overnight in a nitrogen atmosphere, excess potassium hydroxide was treated by adding an aqueous hydrochloric acid solution, and water and AK-225 were added to carry out liquid separation treatment. After washing with water three times, the organic phase was recovered and concentrated by an evaporator to obtain 5.14 g of a methanol adduct. Again into a 50 mL eggplant flask connected to a reflux condenser, 1.0 g of the methanol adduct and 0.13 g of pellets of potassium hydroxide were added, and while heating at 100° C., 10.86 g of the compound (11a) was dropwise added. After stirring for further 9 hours while maintaining the temperature at 100° C., excess potassium hydroxide was treated by adding an aqueous hydrochloric acid solution, and water and AK-225 were added to carry out liquid separation treatment. After washing with water three times, the organic phase was recovered and concentrated by an evaporator to obtain 11 g of an oligomer with a high viscosity. It was diluted again with AK-225 to double and developed and fractionated by silica gel column chromatography (developing solvent: AK-225). With respect to each fraction, an average value of the number of units (n+1) was obtained from the integrated value of $^{19}$F-NMR. 4.76 g of a compound (10a-2i) having fractions with an average value of (n+1) in the following formula (10a-2) being from 7 to 10 put together, was obtained.

$$CH_3—O—(CF_2CFHO—CF_2CF_2CF_2CH_2O)_{n+1}—H \quad (10a-2)$$

NMR spectrum of compound (10a-2i):
$^1$H-NMR (300.4 MHz, solvent: deuterated chloroform, standard: TMS) δ (ppm): 3.7 (3H), 4.0 (2H), 4.4 (14H), 6.0-6.2 (8H)
$^{19}$F-NMR (282.7 MHz, solvent: deuterated chloroform, standard: CFCl$_3$) δ (ppm): −84.7~−87.0 (16F), −89.4~−91.6 (16F), −121.5 (14F), −123.4 (2F), −128.0 (16F), −145.3 (8F)
Average value of the number of units (n+1): 8

Ex. 6-2

Into a 100 mL eggplant flask connected to a reflux condenser, 11.35 g of the compound (10a-2i) obtained in Ex. 6-1, 2.05 g of a sodium fluoride powder and 78 g of AK-225 were introduced, and 9.82 g of CF$_3$CF$_2$CF$_2$OCF(CF$_3$)COF was added. After stirring at 40° C. for 24 hours in a nitrogen atmosphere, stirring was continued at room temperature overnight. After removing the sodium fluoride powder by pressure filtration, excess CF$_3$CF$_2$CF$_2$OCF(CF$_3$)COF and AK-225 were distilled off under reduced pressure. By silica gel column chromatography (developing solvent: AK-225), highly polar impurities were removed to obtain 9.48 g (yield: 75%) of a compound (9a-2i) of the following formula (9a-2) wherein the average value of the number of units (n+1) is 8.

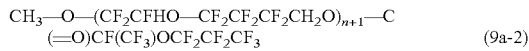

$$CH_3—O—(CF_2CFHO—CF_2CF_2CF_2CH_2O)_{n+1}—C(=O)CF(CF_3)OCF_2CF_2CF_3 \quad (9a-2)$$

NMR spectrum of compound (9a-2i):
$^1$H-NMR (300.4 MHz, solvent: deuterated acetone, standard: TMS) δ (ppm): 3.7 (3H), 4.7 (14H), 5.2 (2H), 6.7-6.9 (8H)
$^{19}$F-NMR (282.7 MHz, solvent: deuterated acetone, standard: CFCl$_3$) δ (ppm): −79.0 (1F), −81.1 (3F), −81.9 (3F), −83.7~−85.0 (16F), −86.0 (1F), −89.0~−92.0 (16F), −119.8 (2F), −120.2 (14F), −126.6 (16F), −129.3 (2F), −131.5 (1F), −145.0 (8F)
Average value of the number of units (n+1): 8

Ex. 6-3

An autoclave (made of nickel, internal capacity: 500 mL) was provided, and at a gas discharge outlet of the autoclave, a condenser held at 0° C., a NaF pellets-packed layer and a condenser held at −10° C. were set in series. Further, a liquid-returning line to return a liquid condensed from the condenser held at −10° C. to the autoclave, was set.

Into the autoclave, 312 g of R-113 was put and stirred while the temperature was maintained at 25° C. After blowing nitrogen gas at 25° C. for one hour into the autoclave, the 20% fluorine gas was blown into it at 25° C. for one hour at a flow rate of 2.0 L/hr. Then, while blowing the 20% fluorine gas at the same flow rate, a solution having 8.4 g of the compound (9a-2i) obtained in Ex. 6-2 dissolved in 84 g of R-113, was injected into the autoclave over a period of 3.6 hours.

Then, while blowing the 20% fluorine gas at the same flow rate, the internal pressure of the autoclave was raised to 0.15 MPa (gauge pressure). Into the autoclave, 9 mL of a benzene solution containing 0.015 g/mL of benzene in R-113, was injected while heating to from 25° C. to 40° C., whereupon the benzene solution injection inlet of the autoclave was closed. After stirring for 15 minutes, 6 mL of the benzene solution was injected again while maintaining the temperature at 40° C., whereupon the injection inlet was closed. The same operation was further repeated 3 times. The total injected amount of benzene was 0.33 g.

Further, stirring was continued for one hour while blowing the 20% fluorine gas at the same flow rate. Then, the internal pressure of the autoclave was adjusted to the atmospheric pressure, and nitrogen gas was injected for one hour. The content in the autoclave was concentrated by an evaporator to obtain 8.8 g (yield: 99%) of a compound (7a-2i) of the following formula (7a-2) wherein the average value of the number of units (n) is 7.

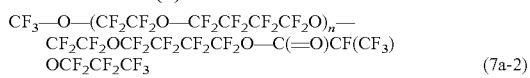

$$CF_3—O—(CF_2CF_2O—CF_2CF_2CF_2CF_2O)_n—CF_2CF_2OCF_2CF_2CF_2CF_2O—C(=O)CF(CF_3)OCF_2CF_2CF_3 \quad (7a-2)$$

NMR spectrum of compound (7a-2i):
$^{19}$F-NMR (282.7 MHz, solvent: deuterated chloroform, standard: CFCl$_3$) δ (ppm): −56.2 (3F), −80.0 (1F), −82.0~−82.5 (6F), −84.1 (30F), −86.7~−87.8 (3F), −89.3 (30F), −91.3 (2F), −126.5 (32F), −130.4 (2F), −132.4 (1F)
Average value of the number of units (n): 7

Ex. 6-4

Into a 50 mL eggplant flask, 8.8 g of the compound (7a-2i) obtained in Ex. 6-3, 0.99 g of sodium fluoride and 10.3 g of AK-225 were put. In a nitrogen atmosphere, 2.1 g of methanol was added, and after stirring at 50° C. for 2 hours, stirring was continued at room temperature overnight. After removing sodium fluoride by pressure filtration, the reaction mixture was concentrated by an evaporator to obtain 8.5 g (yield: 99%) of a precursor (4a-2).

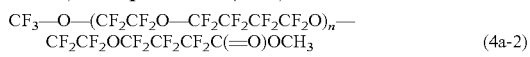

$$CF_3—O—(CF_2CF_2O—CF_2CF_2CF_2CF_2O)_n—CF_2CF_2OCF_2CF_2CF_2C(=O)OCH_3 \quad (4a-2)$$

NMR spectrum of precursor (4a-2):
$^1$H-NMR (300.4 MHz, solvent: deuterated chloroform, standard: TMS) δ (ppm): 3.9 (3H)
$^{19}$F-NMR (282.7 MHz, solvent: deuterated chloroform, standard: CFCl$_3$) δ (ppm): −56.2 (3F), −84.0 (30F), −89.2 (30F), −91.3 (2F), −119.8 (2F), −126.5 (28F), −127.8 (2F)
Average value of the number of units (n): 7

Ex. 6-5

Into a 6 mL screw bottle, 2.02 g of the precursor (4a-2) obtained in Ex. 6-4 and 0.18 g of H$_2$NCH$_2$CH$_2$CH$_2$Si(OCH$_3$)$_3$ were put and stirred for 12 hours. From NMR, it was confirmed that 97% of the precursor (4a-2) was converted to a compound (1-3a-2). Further, all of H$_2$NCH$_2$CH$_2$CH$_2$Si(OCH$_3$)$_3$ was reacted, and methanol was formed as a byproduct. Thus, a composition (F) containing 96% of the compound (1-3a-2), was obtained. The number average molecular weight of the compound (1-3a-2) was 2,900. The results are shown in Table 1.

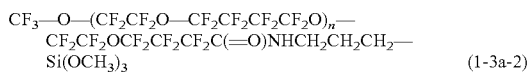

$$CF_3—O—(CF_2CF_2O—CF_2CF_2CF_2CF_2O)_n—CF_2CF_2OCF_2CF_2CF_2C(=O)NHCH_2CH_2CH_2—Si(OCH_3)_3 \quad (1-3a-2)$$

NMR spectrum of compound (1-3a-2):
$^1$H-NMR (300.4 MHz, solvent: deuterated chloroform, standard: TMS) δ (ppm): 0.6 (2H), 1.6 (2H), 2.8 (1H), 3.3 (2H), 3.5 (9H)
$^{19}$F-NMR (282.7 MHz, solvent: deuterated chloroform, standard: CFCl$_3$) δ (ppm): −56.2 (3F), −84.1 (30F), −89.3 (30F), −91.3 (2F), −120.8 (2F), −126.6 (28F), −127.2 (2F)
Average value of the number of units (n): 7

Ex. 7

Production of Mixture (G)

Ex. 7-1

Into a 50 mL two-necked eggplant flask, 0.07 g of aluminum lithium hydride was suspended in 2.7 g of THF. While cooling in an ice bath, a solution having 6.1 g of the precursor (4a-2) obtained in Ex. 6-4, i.e. the compound (6a-2), diluted with 6.0 g of AC-6000 (tradename, manufactured by Asahi Glass Company, Limited), was slowly dropwise added. Thereafter, the ice bath was removed, and stirring was continued while raising the temperature slowly to room temperature. After stirring at room temperature for 12 hours, an aqueous hydrochloric acid solution was dropwise added until the liquid became acidic. 15 mL of AK-225 was added, and after washing once with water and once with a saturated sodium chloride aqueous solution, the organic phase was recovered. The recovered organic phase was concentrated by an evaporator to obtain 5.9 g (yield: 97%) of a compound (5a-2).

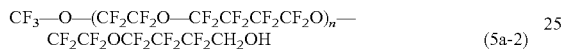
(5a-2)

NMR spectrum of compound (5a-2):
$^1$H-NMR (300.4 MHz, solvent: deuterated chloroform, standard: TMS) δ (ppm): 2.0 (1H), 4.0 (2H)
$^{19}$F-NMR (282.7 MHz, solvent: deuterated chloroform, standard: CFCl$_3$) δ (ppm): −56.2 (3F), −84.1 (30F), −89.3 (28F), −91.4 (2F), −123.7 (2F), −126.6 (28F), −128.7 (2F)
Average value of the number of units (n): 7

Ex. 7-2

Into a 50 mL two-necked eggplant flask, 0.11 g of sodium hydride was suspended in 1.1 g of THF. A solution having 5.9 g of the compound (5a-2) obtained in Ex. 7-1 diluted with 10 g of AC-6000 was dropwise added thereto, and further, 1.1 g of allyl bromide was dropwise added. The mixture was adjusted to 70° C. in an oil bath and stirred for 5 hours. 5 mL of AK-225 was added, and the mixture was washed once with water and once with a saturated sodium chloride aqueous solution, whereupon the organic phase was recovered. The recovered organic phase was passed through a silica gel column, and the recovered solution was concentrated by an evaporator and washed three times with hexane to obtain 3.8 g (yield: 63%) of a precursor (3Ha-2).

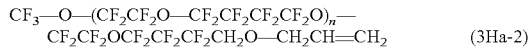
(3Ha-2)

NMR spectrum of precursor (3Ha-2):
$^1$H-NMR (300.4 MHz, solvent: deuterated chloroform, standard: TMS) δ (ppm): 3.8 (2H), 4.1 (2H), 5.2 (2H), 5.9 (2H)
$^{19}$F-NMR (282.7 MHz, solvent: deuterated chloroform, standard: CFCl$_3$) δ (ppm): −56.2 (3F), −84.1 (30F), −89.3 (30F), −91.4 (2F), −120.5 (2F), −126.6 (28F), −128.6 (2F)
Average value of the number of units (n): 7

Ex. 7-3

Into a 50 mL closed type pressure resistant container made of PTFE, 3.6 g of the precursor (3Ha-2) obtained in Ex. 7-2, 0.03 g of di-tert-butyl peroxide, 1.1 g of trichlorosilane and 3.6 g of HFE-7300 were put and stirred at 120° C. for 8 hours. After distilling off unreacted substances, solvent, etc. by concentration under reduced pressure, the reaction mixture was put into a flask equipped with a dropping funnel, and 5 g of 1,3-bis(trifluoromethyl)benzene was put, followed by stirring at room temperature. 1.0 g of a mixed solution of trimethyl orthoformate and methanol (trimethyl orthoformate:methanol=25:1 [mol:mol]) was dropwise added and reacted at 60° C. for 3 hours. After completion of the reaction, the solvent, etc. were distilled off under reduced pressure, and to the residue, 0.05 g of activated carbon was added, followed by stirring for one hour, and then, filtration was carried out by means of a membrane filter with a pore diameter of 0.5 μm to obtain 3.0 g (yield: 81%) of a mixture (G) of a compound (1-1Ha-2) and a compound (1-2Ha-2). The molar ratio of the compound (1-1Ha-2) to the compound (1-2Ha-2) was 90:10 from NMR. The number average molecular weight of the mixture (G) was 4,900. The results are shown in Table 1.

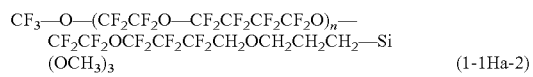
(1-1Ha-2)

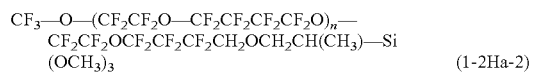
(1-2Ha-2)

NMR spectrum of compound (1-1Ha-2):
$^1$H-NMR (300.4 MHz, solvent: deuterated chloroform, standard: TMS) δ (ppm): 0.7 (2H), 1.7 (2H), 3.6 (11H), 3.8 (2H)
$^{19}$F-NMR (282.7 MHz, solvent: deuterated chloroform, standard: CFCl$_3$) δ (ppm): −56.2 (3F), −84.1 (30F), −89.3 (30F), −91.4 (2F), −120.7 (2F), −126.6 (28F), −128.6 (2F)
NMR spectrum of compound (1-2Ha-2):
$^1$H-NMR (300.4 MHz, solvent: deuterated chloroform, standard: TMS) δ (ppm): 1.1 (3H), 1.8 (1H), 3.6 (11H), 3.8 (2H)
$^{19}$F-NMR (282.7 MHz, solvent: deuterated chloroform, standard: CFCl$_3$) δ (ppm): −56.2 (3F), −84.1 (30F), −89.3 (30F), −91.4 (2F), −120.7 (2F), −126.6 (28F), −128.6 (2F)
Average value of the number of units (n): 7

Ex. 8

Production of Composition (H)

Ex. 8-1

Into a 500 mL three-necked round-bottomed flask, 28.2 g of a sodium borohydride powder was put, and 150 g of AK-225 was added. While cooling and stirring in an ice bath, a solution having 300 g of a compound (12b), 45.5 g of methanol and 100 g of AK-225 mixed, was slowly dropwise added from a dropping funnel in a nitrogen atmosphere so that the internal temperature would not exceed 10° C. After dropwise addition of the entire amount, a solution having 30 g of methanol and 30 g of AK-225 mixed, was dropwise added. Then, the ice bath was removed, and while raising the temperature slowly to room temperature, stirring was continued. After stirring at room temperature overnight, the reaction mixture was cooled again in an ice bath, and an aqueous hydrochloric acid solution was dropwise added until the liquid became acidic. After completion of the reaction, the reaction mixture was washed once with water and once with a saturated aqueous sodium chloride solution, whereupon an organic phase was recovered. The recovered organic phase was dried over magnesium sulfate, and then, the solid content was filtered off, and the filtrate was concentrated by an evaporator. The recovered concentrated liquid was distilled under reduced pressure to obtain 262.6 g (yield: 94%) of a compound (11b).

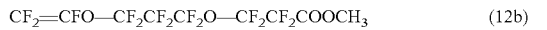

$CF_2=CFO-CF_2CF_2CF_2O-CF_2CF_2COOCH_3$ (12b)

$CF_2=CFO-CF_2CF_2CF_2O-CF_2CF_2CH_2OH$ (11b)

NMR spectrum of compound (11b):
$^1$H-NMR (300.4 MHz, solvent: deuterated chloroform, standard: TMS) δ (ppm): 2.1 (1H), 4.1 (2H)
$^{19}$F-NMR (282.7 MHz, solvent: deuterated chloroform, standard: CFCl$_3$) δ (ppm): −83.8 (2F), −85.4 (2F), −86.2 (2F), −113.1 (1F), −121.6 (1F), −126.5 (2F), −129.2 (2F), −135.1 (1F)

Ex. 8-2

Into a 100 mL eggplant flask connected to a reflux condenser, 31.0 g of the compound (11b) obtained in Ex. 8-1, and 1.1 g of TFEO were introduced, and 1.5 g of a potassium carbonate powder was added. After stirring at 50° C. for 3 hours in a nitrogen atmosphere, stirring was carried out at 60° C. for 8 hours, and further continued at room temperature overnight. Excess potassium carbonate was treated by adding an aqueous hydrochloric acid solution, and water and AK-225 were added to carry out liquid separation treatment. After washing with water three times, the organic phase was recovered and concentrated by an evaporator to obtain 32.0 g of an oligomer with a high viscosity. It was diluted again with AK-225 to double and developed and fractionated by silica gel column chromatography (developing solvent: AK-225). With respect to each fraction, an average value of the number of units (n+1) was obtained from the integrated value of $^{19}$F-NMR. 8.3 g of a compound (10b-1) having fractions with an average value of (n+1) being from 5 to 8 put together, was obtained.

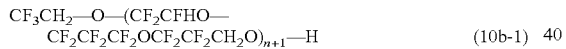

$CF_3CH_2-O-(CF_2CFHO-CF_2CF_2CF_2OCF_2CF_2CH_2O)_{n+1}-H$ (10b-1)

NMR spectrum of compound (10b-1):
$^1$H-NMR (300.4 MHz, solvent: deuterated acetone, standard: TMS) δ (ppm): 4.1 (2H), 4.7 (12H), 6.7-6.9 (6H)
$^{19}$F-NMR (282.7 MHz, solvent:deuterated acetone, standard: CFCl$_3$) δ (ppm): −74.2 (3F), −83.3 (12F), −84.1~−85.0 (12F), −85.3 (12F), −89.6~−90.6 (12F), −123.5 (2F), −125.3 (10F), −128.8 (12F), −145.3 (6F)
Average value of the number of units (n+1): 6

Ex. 8-3

Into a 100 mL eggplant flask connected to a reflux condenser, 8.31 g of the compound (10b-1) obtained in Ex. 8-2, 1.86 g of a sodium fluoride powder and 25.13 g of AK-225 were introduced, and 9.68 g of CF$_3$CF$_2$CF$_2$OCF(CF$_3$)COF was added. In a nitrogen atmosphere, stirring was carried out at 40° C. for 10 hours. After removing the sodium fluoride powder by pressure filtration, excess CF$_3$CF$_2$CF$_2$OCF(CF$_3$)COF and AK-225 were distilled off under reduced pressure. By silica gel column chromatography (developing solvent: AK-225), highly polar impurities were removed to obtain 9.38 g (yield: 99%) of a compound (9b-1).

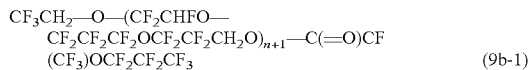

$CF_3CH_2-O-(CF_2CHFO-CF_2CF_2CF_2OCF_2CF_2CH_2O)_{n+1}-C(=O)CF(CF_3)OCF_2CF_2CF_3$ (9b-1)

NMR spectrum of compound (9b-1):
$^1$H-NMR (300.4 MHz, solvent: deuterated acetone, standard: TMS) δ (ppm): 4.7 (12H), 5.3 (2H), 6.7-6.9 (6H)
$^{19}$F-NMR (282.7 MHz, solvent: deuterated acetone, standard: CFCl$_3$) δ (ppm): −74.3 (3F), −79.2 (1F), −81.1 (3F), −81.9 (3F), −83.3 (12F), −83.6~−85.0 (12F), −85.3 (12F), −86.0 (1F), −89.4~−90.6 (12F), −123.0 (2F), −123.4 (10F), −128.8 (12F), −129.4 (2F), −131.5 (1F), −145.3 (6F)
Average value of the number of units (n+1): 6

Ex. 8-4

An autoclave (made of nickel, internal capacity: 500 mL) was provided, and at a gas discharge outlet of the autoclave, a condenser held at 0° C., a NaF pellets-packed layer and a condenser held at −10° C. were set in series. Further, a liquid-returning line to return a liquid condensed from the condenser held at −10° C. to the autoclave, was set.

Into the autoclave, 312 g of R-113 was put and stirred while maintaining the temperature at 25° C. After blowing nitrogen gas at 25° C. for one hour into the autoclave, the 20% fluorine gas was blown into it at 25° C. for one hour at a flow rate of 1.4 L/hr. Then, while blowing the 20% fluorine gas at the same flow rate, a solution having 8.9 g of the compound (9b-1) obtained in Ex. 8-3 dissolved in 89 g of R-113, was injected into the autoclave over a period of 4 hours.

Then, while blowing the 20% fluorine gas at the same flow rate, the internal pressure of the autoclave was raised to 0.15 MPa (gauge pressure). Into the autoclave, 9 mL of a benzene solution containing 0.015 g/mL of benzene in R-113, was injected while heating to from 25° C. to 40° C., whereupon the benzene solution injection inlet of the autoclave was closed. After stirring for 15 minutes, 6 mL of the benzene solution was injected again while maintaining the temperature at 40° C., whereupon the injection inlet was closed. The same operation was further repeated 3 times. The total injected amount of benzene was 0.33 g.

Further, stirring was continued for one hour while blowing the 20% fluorine gas at the same flow rate. Then, the internal pressure of the autoclave was adjusted to the atmospheric pressure, and nitrogen gas was injected for one hour. The content in the autoclave was concentrated by an evaporator to obtain 10.4 g (yield: 99%) of a compound (7b-1).

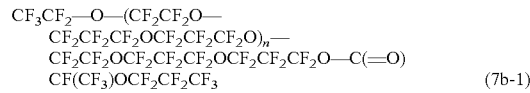

$CF_3CF_2-O-(CF_2CF_2O-CF_2CF_2CF_2OCF_2CF_2CF_2O)_n-CF_2CF_2OCF_2CF_2CF_2OCF_2CF_2CF_2O-C(=O)CF(CF_3)OCF_2CF_2CF_3$ (7b-1)

NMR spectrum of compound (7b-1):
$^{19}$F-NMR (282.7 MHz, solvent: deuterated acetone, standard: CFCl$_3$) δ (ppm): −80.0 (1F), −82.5 (3F), −82.8 (3F), −84.3 (46F), −86.7~−88.1 (6F), −89.4 (24F), −129.8 (2F), −130.2 (24F), −130.6 (2F), −132.4 (1F)
Average value of the number of units (n): 5

Ex. 8-5

Into a 50 mL eggplant flask, 10.4 g of the compound (7b-1) obtained in Ex. 8-4, 0.68 g of sodium fluoride and 13.72 g of AK-225 were put. In a nitrogen atmosphere, 2.0 of methanol was added, and after stirring at 50° C. for 2 hours, stirring was continued at room temperature overnight. After removing sodium fluoride by pressure filtration, the reaction mixture was concentrated by an evaporator to obtain 9.0 g (yield: 99%) of a precursor (4b-1).

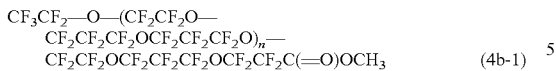
(4b-1)

NMR spectrum of precursor (4b-1):
$^1$H-NMR (300.4 MHz, solvent: deuterated acetone, standard: TMS) δ (ppm): 3.9 (3H)
$^{19}$F-NMR (282.7 MHz, solvent: deuterated acetone, standard: CFCl$_3$) δ (ppm): −84.3 (44F), −86.4 (2F), −88.1 (3F), −89.4 (26F), −122.4 (2F), −130.2 (22F)
Average value of the number of units (n): 5

Ex. 8-6

Into a 6 mL screw bottle, 1.43 g of the precursor (4b-1) obtained in Ex. 8-5 and 0.12 g of H$_2$NCH$_2$CH$_2$CH$_2$Si(OCH$_3$)$_3$ were put and stirred for 12 hours. From NMR, it was confirmed that 97% of the precursor (4b-1) was converted to a compound (1-3b-1). Further, all of H$_2$NCH$_2$CH$_2$CH$_2$Si(OCH$_3$)$_3$ was reacted, and methanol was formed as a byproduct. Thus, a composition (H) containing 96% of the compound (1-3b-1), was obtained. The number average molecular weight of the compound (1-3b-1) was 3,000. The results are shown in Table 1.

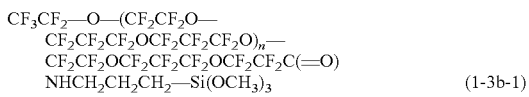
(1-3b-1)

NMR spectrum of compound (1-3b-1):
$^1$H-NMR (300.4 MHz, solvent: deuterated chloroform, standard: TMS) δ (ppm): 0.7 (2H), 1.7 (2H), 2.8 (1H), 3.4 (2H), 3.5 (9H)
$^{19}$F-NMR (282.7 MHz, solvent: deuterated chloroform, standard: CFCl$_3$) δ (ppm): −84.1 (44F), −85.7 (2F), −87.9 (3F), −89.2 (26F), −123.5 (2F), −129.9 (22F)
Average value of the number of units (n): 5

Ex. 9

Production of Mixture (I)

Ex. 9-1

Into a 50 mL two-necked eggplant flask, 0.09 g of aluminum lithium hydride was suspended in 3.6 g of THF. While cooling in an ice bath, a solution having 6.8 g of the precursor (4b-1) obtained in Ex. 8-5, i.e. the compound (6b-1), diluted with 7.0 g of AC-6000, was slowly dropwise added. Thereafter, the ice bath was removed, and stirring was continued while raising the temperature slowly to room temperature. After stirring at room temperature for 12 hours, an aqueous hydrochloric acid solution was dropwise added until the liquid became acidic. 15 mL of AK-225 was added, and after washing once with water and once with a saturated sodium chloride aqueous solution, the organic phase was recovered. The recovered organic phase was concentrated by an evaporator to obtain 6.6 g (yield: 99%) of a compound (5b-1).

(5b-1)

NMR spectrum of compound (5b-1):
$^1$H-NMR (300.4 MHz, solvent: deuterated chloroform, standard: TMS) δ (ppm): 1.8 (1H), 4.0 (2H)

$^{19}$F-NMR (282.7 MHz, solvent: deuterated chloroform, standard: CFCl$_3$) δ (ppm): −84.1 (44F), −86.5 (2F), −87.7 (3F), −89.2 (26F), −127.0 (2F), −129.9 (22F)
Average value of the number of units (n): 5

Ex. 9-2

Into a 50 mL two-necked eggplant flask, 0.15 g of sodium hydride was suspended in 1.5 g of THF. A solution having 6.3 g of the compound (5b-1) obtained in Ex. 9-1 diluted with 11.6 g of AC-6000 was dropwise added thereto, and further, 1.35 g of allyl bromide was dropwise added. The mixture was adjusted to 70° C. in an oil bath and stirred for 5 hours. 5 mL of AK-225 was added, and the mixture was washed once with water and once with a saturated sodium chloride aqueous solution, whereupon the organic phase was recovered. The recovered organic phase was passed through a silica gel column, and the recovered solution was concentrated by an evaporator and washed three times with hexane to obtain 5.4 g (yield: 84%) of a precursor (3Hb-1).

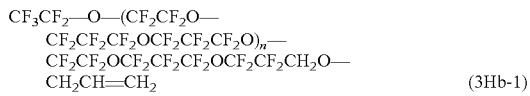
(3Hb-1)

NMR spectrum of precursor (3Hb-1):
$^1$H-NMR (300.4 MHz, solvent: deuterated chloroform, standard: TMS) δ (ppm): 3.8 (2H), 4.1 (2H), 5.2 (2H), 5.8 (2H)
$^{19}$F-NMR (282.7 MHz, solvent: deuterated chloroform, standard: CFCl$_3$) δ (ppm): −84.1 (44F), −86.4 (2F), −87.7 (3F), −89.2 (26F), −123.7 (2F), −129.9 (22F)
Average value of the number of units (n): 5

Ex. 9-3

Into a 50 mL closed type pressure resistant container made of PTFE, 5.5 g of the precursor (3Hb-1) obtained in Ex. 9-2, 0.03 g of di-tert-butyl peroxide, 2.1 g of trichlorosilane and 5.5 g of HFE-7300 were put and stirred at 120° C. for 8 hours. After distilling off unreacted substances, solvent, etc. by concentration under reduced pressure, the reaction mixture was put into a flask equipped with a dropping funnel, and 5 g of 1,3-bis(trifluoromethyl)benzene was put, followed by stirring at room temperature. 1.8 g of a mixed solution of trimethyl orthoformate and methanol (trimethyl orthoformate:methanol=25:1 [mol:mol]) was dropwise added and reacted at 60° C. for 3 hours. After completion of the reaction, the solvent, etc. were distilled off under reduced pressure, and to the residue, 0.05 g of activated carbon was added, followed by stirring for one hour, and then, filtration was carried out by means of a membrane filter with a pore diameter of 0.5 μm to obtain 4.6 g (yield: 80%) of a mixture (I) of a compound (1-1Hb-1) and a compound (1-2Hb-1). The molar ratio of the compound (1-1Hb-1) to the compound (1-2Hb-1) was 92:8 from NMR. The number average molecular weight of the mixture (I) was 3,000. The results are shown in Table 1.

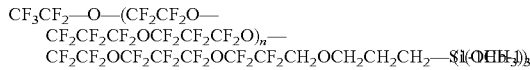

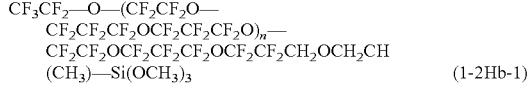
(1-2Hb-1)

NMR spectrum of compound (1-1Hb-1):

$^{1}$H-NMR (300.4 MHz, solvent: deuterated chloroform, standard: TMS) δ (ppm): 0.7 (2H), 1.7 (2H), 3.6 (11H), 3.8 (2H)

$^{19}$F-NMR (282.7 MHz, solvent: deuterated chloroform, standard: CFCl$_3$) δ (ppm): −84.1 (44F), −86.4 (2F), −87.7 (3F), −89.2 (26F), −123.8 (2F), −129.9 (22F)

NMR spectrum of compound (1-2Hb-1):

$^{1}$H-NMR (300.4 MHz, solvent: deuterated chloroform, standard: TMS) δ (ppm): 1.1 (3H), 1.8 (1H), 3.6 (11H), 3.8 (2H)

$^{19}$F-NMR (282.7 MHz, solvent: deuterated chloroform, standard: CFCl$_3$) δ (ppm): −84.1 (44F), −86.4 (2F), −87.7 (3F), −89.2 (26F), −123.8 (2F), −129.9 (22F)

Average value of the number of units (n): 5

Ex. 10

Production of Compound (J)

A fluorinated ether compound constituted by a combination of (CF$_2$O) and (CF$_2$CF$_2$O) was synthesized in accordance with the method disclosed in U.S. Pat. No. 5,258,110 and U.S. Pat. No. 3,847,978. The acid fluoride (—COF) terminal of the obtained fluorinated ether compound was esterified by a reaction with an alcohol, and an aminopropylsilane compound was reacted to convert the terminal to a hydrolysable trimethoxysilyl group thereby to obtain the compound (J).

Ex. 11

Production of Mixture (K)

Ex. 11-1

Into a 1 L three-necked flask connected to a reflux condenser, 37.61 g of methanol was introduced, and 54.02 g of a potassium carbonate powder was added. While stirring at 120° C. in a nitrogen atmosphere, 2,400 g of the compound (11a) obtained in Ex. 1-1 was slowly dropwide added. After dropwise addition of the entire amount, stirring was continued for further one hour while maintaining the temperature at 120° C., whereupon heating was terminated, and stirring was continued until the temperature dropped to room temperature. Excess potassium carbonate was treaded by adding an aqueous hydrochloric acid solution, and water and AK-225 were added to carry out liquid separation treatment. After washing three times with water, an organic phase was recovered and concentrated by an evaporator to obtain 2,406 g of an oligomer with a high viscosity. It was diluted again with AK-225 to double and developed and fractionated by silica gel column chromatography (developing solvent: AK-225). With respect to each fraction, an average value of the number of units (n+1) was obtained from the integrated value of $^{19}$F-NMR. 514.4 g (yield: 21%) of a compound (10a-2ii) having fractions with an average value of (n+1) in the above formula (10a-2) being from 13 to 16 put together, was obtained.

NMR spectrum of compound (10a-2ii):

$^{1}$H-NMR (300.4 MHz, solvent: deuterated chloroform, standard: TMS) δ (ppm): 3.7 (3H), 4.0 (2H), 4.4 (26H), 6.0~6.2 (14H)

$^{19}$F-NMR (282.7 MHz, solvent: deuterated chloroform, standard: CFCl$_3$) δ (ppm): −84.7~−87.0 (28F), −89.4~−91.6 (28F), −121.5 (26F), −123.4 (2F), −128.0 (28F), −145.3 (14F)

Average value of the number of units (n+1): 14

Ex. 11-2

Into a 300 mL three-necked flask connected to a reflux condenser, 192.6 g of the compound (10a-2ii) obtained in Ex. 11-1, and 24.35 g of a sodium fluoride powder were introduced, and 80.3 g of CF$_3$CF$_2$CF$_2$OCF(CF$_3$)COF was added. After stirring at 40° C. for 24 hours in a nitrogen atmosphere, stirring was continued at room temperature overnight. After removing the sodium fluoride powder by pressure filtration, excess CF$_3$CF$_2$CF$_2$OCF(CF$_3$)COF was distilled off under reduced pressure. By silica gel column chromatography (developing solvent: AK-225), highly polar impurities were removed to obtain 195.4 g (yield: 94%) of a compound (9a-2ii) of the above formula (9a-2) wherein the average value of the number of units (n+1) is 14.

NMR spectrum of compound (9a-2ii):

$^{1}$H-NMR (300.4 MHz, solvent: deuterated acetone, standard: TMS) δ (ppm): 3.7 (3H), 4.7 (26H), 5.2 (2H), 6.7-6.9 (14H)

$^{19}$F-NMR (282.7 MHz, solvent: deuterated acetone, standard: CFCl$_3$) δ (ppm): −79.0 (1F), −81.1 (3F), −81.9 (3F), −83.7~−85.0 (28F), −86.0 (1F), −89.0~−92.0 (28F), −119.8 (2F), −120.2 (26F), −126.6 (28F), −129.3 (2F), −131.5 (1F), −145.0 (14F)

Average value of the number of units (n+1): 14

Ex. 11-3

An autoclave (made of nickel, internal capacity: 1 L) was provided, and at a gas discharge outlet of the autoclave, a condenser held at 20° C., a NaF pellets-packed layer and a condenser held at 0° C. were set in series. Further, a liquid-returning line to return a liquid condensed from the condenser held at 0° C. to the autoclave, was set.

Into the autoclave, 750 g of ClCF$_2$CFClCF$_2$OCF$_2$CF$_2$Cl (hereinafter referred to as CFE-419) was put and stirred while maintaining the temperature at 25° C. After blowing nitrogen gas at 25° C. for one hour into the autoclave, the 20% fluorine gas was blown into it at 25° C. for one hour at a flow rate of 3.6 L/hr. While blowing the 20% fluorine gas at the same flow rate, a solution having 107.0 g of the compound (9a-2ii) obtained in Ex. 11-2 dissolved in 370 g of CFE-419, was injected into the autoclave over a period of 17.3 hours.

Then, while blowing the 20% fluorine gas at the same flow rate, the internal pressure of the autoclave was raised to 0.15 MPa (gauge pressure). Into the autoclave, 4 mL of a benzene solution containing 0.05 g/mL of benzene in CFE-419, was injected while heating to from 25° C. to 40° C., whereupon the benzene solution injection inlet of the autoclave was closed. After stirring for 15 minutes, 4 mL of the benzene solution was injected again while maintaining the temperature at 40° C., whereupon the injection inlet was closed. The same operation was further repeated 3 times. The total injected amount of benzene was 0.17 g.

Further, stirring was continued for one hour while blowing the 20% fluorine gas at the same flow rate. Then, the internal pressure of the autoclave was adjusted to the atmospheric pressure, and nitrogen gas was injected for one hour. The content in the autoclave was concentrated by an evaporator to obtain 122.5 g (yield: 97%) of a compound (7a-2ii) of the above formula (7a-2) wherein the average value of the number of units (n) is 13.

NMR spectrum of compound (7a-2ii):

$^{19}$F-NMR (282.7 MHz, solvent: deuterated chloroform, standard: CFCl$_3$) δ (ppm): −56.2 (3F), −80.0 (1F), −82.0~−82.5 (6F), −84.1 (54F), −86.7~−87.8 (3F), −89.3 (54F), −91.3 (2F), −126.5 (56F), −130.4 (2F), −132.4 (1F)

Average value of the number of units (n): 13

Ex. 11-4

Into a 100 mL three necked flask equipped with a Liebig condenser, 60.0 g of the compound (7a-2ii) obtained in Ex. 11-3 and 0.15 g of potassium fluoride were put. In a nitrogen atmosphere, stirring was carried out at 80° C. for 2 hours. Further, under reduced pressure, CF$_3$CF$_2$CF$_2$OCF(CF$_3$)C(=O)F formed as a byproduct was distilled off. Potassium fluoride was removed by a pressure filter to obtain 54.6 g of (yield: 98%) of a compound (8a-2).

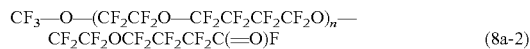

(8a-2)

NMR spectrum of compound (8a-2):

$^1$H-NMR (300.4 MHz, solvent: deuterated chloroform, standard: TMS) δ (ppm): 3.9 (3H)

$^{19}$F-NMR (282.7 MHz, solvent: deuterated chloroform, standard: CFCl$_3$) δ (ppm): 24.0 (1F), −56.2 (3F), −84.7 (54F), −89.1 (54F), −90.1 (2F), −119.1 (2F), −126.5 (52F), −127.3 (2F)

Average value of the number of units (n): 13

Ex. 11-5

Into a 100 mL three necked flask equipped with a reflux condenser, 54.5 g of the compound (8a-2) obtained in Ex. 11-4 and 2.5 g of lithium iodide were put, and stirred at 180° C. for 10 hours. From the reaction crude liquid, a solid content was collected by filtration to obtain 53.2 g of a product. This product was a mixture of a desired compound (15a-1) and a byproduct compound (18a-1) (a compound of the formula (1) wherein B is represented by the formula (2-9)), and their molar ratio was 90:10 from NMR.

CF$_3$—O—(CF$_2$CF$_2$O—CF$_2$CF$_2$CF$_2$CF$_2$O)$_n$—CF$_2$CF$_2$OCF$_2$CF$_2$CF$_2$I  (15a-1)

CF$_3$—O—(CF$_2$CF$_2$O—CF$_2$CF$_2$CF$_2$CF$_2$O)$_n$—CF$_2$CF$_2$OCF$_2$CF$_2$CF$_2$H  (18a-1)

NMR spectrum of mixture of compound (15a-1) and (18a-1):

$^1$H-NMR (300.4 MHz, solvent: deuterated chloroform, standard: TMS) δ (ppm): 6.1 (0.1H)

$^{19}$F-NMR (282.7 MHz, solvent: deuterated chloroform, standard: CFCl$_3$) δ (ppm): −56.2 (3F), −59.8 (1.8F), −82.0 (1.8F), −84.7 (52F), −89.1 (54F), −90.1 (2F), −117.6 (1.8F), −126.5 (52F), −133.0 (0.2F), −138.0 (0.2F)

Average value of the number of units (n): 13

Ex. 11-6

Into a 30 mL autoclave made of SUS, 30.0 g of the mixture of the compound (15a-1) and the compound (18a-1) obtained in Ex. 11-5, 0.058 g of an azo-type initiator V-59 (tradename, manufactured by Wako Pure Chemical Industries, Ltd.) and 5.0 g of CFE-419 were put. The reactor was closed and deaerated until the internal pressure of the reactor became −0.099 MPa (G), whereupon ethylene was injected until the internal pressure of the reactor became 1.50 MPa (G). Then, stirring was carried out at 80° C. for 5 hours. By distilling off CFE-419 from the reaction crude liquid, 30.2 g of a product was obtained. This product was a mixture of a desired compound (16a-1) and the compound (18a-1), and their molar ratio was 90:10 from NMR.

(16a-1)

NMR spectrum of mixture of compound (16a-1) and (18a-1):

$^1$H-NMR (300.4 MHz, solvent: deuterated chloroform, standard: TMS) δ (ppm): 2.7 (1.8H), 3.2 (1.8H), 5.9 (0.1H)

$^{19}$F-NMR (282.7 MHz, solvent: deuterated chloroform, standard: CFCl$_3$) δ (ppm): −56.2 (3F), −84.1 (54F), −89.3 (54F), −91.3 (2F), −116.2 (1.8F), −126.5 (52F), −127.6 (1.8F), −133.3 (0.2F), −138.0 (0.2F)

Average value of the number of units (n): 13

Ex. 11-7

Into a 50 mL eggplant flask connected to a reflux condenser, 29.2 g of a mixture of the compound (16a-1) and the compound (18a-1) obtained in Ex. 11-6, 8.8 g of 10 mass % potassium hydroxide and 14.6 g of 1,3-bis(trifluoromethyl)benzene were put, and stirred at 80° C. for 5 hours. After washing with water three times, the organic phase was recovered and concentrated by an evaporator to obtain 28.2 g of a product. This product was a mixture of a desired precursor (13a-1) and the compound (18a-1), and their molar ratio was 90:10 from NMR.

CF$_3$—O—(CF$_2$CF$_2$O—CF$_2$CF$_2$CF$_2$CF$_2$O)$_n$—CF$_2$CF$_2$OCF$_2$CF$_2$CF$_2$CH=CH$_2$  (13a-1)

NMR spectrum of mixture of precursor (13a-1) and (18a-1):

$^1$H-NMR (300.4 MHz, solvent: deuterated chloroform, standard: TMS) δ (ppm): 5.7-6.0 (2.8H)

$^{19}$F-NMR (282.7 MHz, solvent: deuterated chloroform, standard: CFCl$_3$) δ (ppm): −56.2 (3F), −84.1 (54F), −89.3 (54F), −91.3 (2F), −115.2 (1.8F), −126.5 (52F), −128.1 (1.8F), −133.3 (0.2F), −138.0 (0.2F)

Average value of the number of units (n): 13

Ex. 11-8

Into a 50 mL closed type pressure resistant container made of PTFE, 2.0 g of the mixture of the precursor (13a-1) and the compound (18a-1) obtained in Ex. 11-7, 0.015 g of a platinum/1,3-divinyl-1,1,3,3-tetramethyldisiloxane complex xylene solution (platinum content: 2%), 0.13 g of trichlorosilane and 2.0 g of 1,3-bis(trifluoromethyl)benzene were put and stirred at room temperature for 24 hours. After distilling off unreacted substances, solvent, etc. by concentration under reduced pressure, the reaction mixture was put into a flask equipped with a dropping funnel, and 5 g of 1,3-bis(trifluoromethyl)benzene was put, followed by stirring at room temperature. 0.75 g of a mixed solution of trimethyl orthoformate and methanol (trimethyl orthoformate:methanol=25:1 [mol:mol]) was dropwise added and reacted at 60° C. for 3 hours. After completion of the reaction, the solvent, etc. were distilled off under reduced pressure, and to the residue, 0.1 g of activated carbon was added, followed by stirring for one hour, and then, filtration was carried out by means of a membrane filter with a pore diameter of 0.5 μm to obtain 1.9 g (yield: 93%) of a mixture (K) of a compound (1-4a-1), the compound (18a-1) and a byproduct compound (17a-1) (a compound of the formula (1) wherein B is represented by the formula (2-7)). The molar ratio of the compound (1-4a-1), the compound (18a-1) and the compound (17a-1) was 75:10:15 from NMR. The number average molecular weight of the mixture (K) was 4,800. The results are shown in Table 1.

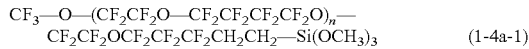  (1-4a-1)

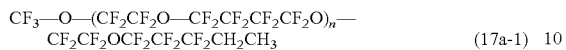  (17a-1)

NMR spectrum of mixture (K):

$^1$H-NMR (300.4 MHz, solvent: deuterated chloroform, standard: TMS) δ (ppm): 0.8 (1.5H), 1.1 (0.45H), 2.1 (1.8H), 3.6 (8.1H), 5.9 (0.1H)

$^{19}$F-NMR (282.7 MHz, solvent: deuterated chloroform, standard: CFCl$_3$) δ (ppm): −56.2 (3F), −84.1 (54F), −89.3 (54F), −91.3 (2F), −117.8 (1.8F), −126.6 (52F), −127.8 (1.8F), −133.3 (0.2F), −138.0 (0.2F)

Average value of the number of units (n): 13

Ex. 12

Method for Production of Mixture (L)

Ex. 12-1

Into a 50 mL eggplant flask, 10.0 g of the mixture of the compound (15a-1) and the compound (18a-1) obtained in Ex. 11-5, 0.015 g of an azo-type initiator V-60 (tradename, manufactured by Wako Pure Chemical Industries, Ltd.), 3.73 g of allyl tributyl tin and 10.0 g of 1,3-bis(trifluoromethyl)benzene were put and stirred at 90° C. for 6 hours. The reaction crude liquid was washed with hexane three times and with acetone three times, whereupon the lower layer was recovered. The recovered lower layer was passed through a silica gel column, and the recovered solution was concentrated by an evaporator to obtain 9.0 g of a product. This product was a mixture of a desired precursor (14a-1) and the compound (18a-1), and their molar ratio was 90:10 from NMR.

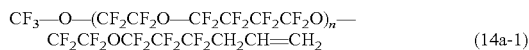  (14a-1)

NMR spectrum of mixture of precursor (14a-1) and compound (18a-1):

$^1$H-NMR (300.4 MHz, solvent: deuterated chloroform, standard: TMS) δ (ppm): 2.8 (1.8H), 5.3 (1.8H), 5.8-5.9 (1.0H)

$^{19}$F-NMR (282.7 MHz, solvent: deuterated chloroform, standard: CFCl$_3$) δ (ppm): −56.2 (3F), −84.1 (54F), −89.3 (54F), −91.4 (2F), −114.4 (1.8F), −126.6 (52F), −127.4 (1.8F), −133.3 (0.2F), −138.0 (0.2F)

Average value of the number of units (n): 13

Ex. 12-2

Into a 50 mL closed type pressure resistant container made of PTFE, 2.0 g of the mixture of the precursor (14a-1) and the compound (18a-1) obtained in Ex. 12-1, 0.011 g of a platinum/1,3-divinyl-1,1,3,3-tetramethyldisiloxane complex xylene solution (platinum content: 2%), 0.53 g of trimethoxysilane and 2.0 g of 1,3-bis(trifluoromethyl)benzene were put and stirred at 80° C. for 12 hours. After completion of the reaction, the solvent, etc. were distilled off under reduced pressure, and to the residue, 0.1 g of activated carbon was added, followed by stirring for one hour, and then, filtration was carried out by means of a membrane filter with a pore diameter of 0.5 μm to obtain 2.0 g (yield: 98%) of a mixture (L) of a compound (1-5a-1) and the compound (18a-1). The molar ratio of the compound (1-5a-1) to the compound (18a-1) was 90:10 from NMR. The number average molecular weight of the mixture (L) was 4,800. The results are shown in Table 1.

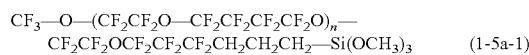  (1-5a-1)

NMR spectrum of mixture (L):

$^1$H-NMR (300.4 MHz, solvent: deuterated chloroform, standard: TMS) δ (ppm): 0.7 (1.8H), 1.7 (1.8H), 2.1 (1.8H), 3.6 (8.1H), 5.9 (0.1H)

$^{19}$F-NMR (282.7 MHz, solvent: deuterated chloroform, standard: CFCl$_3$) δ (ppm): −56.2 (3F), −84.1 (54F), −89.3 (54F), −91.3 (2F), −115.5 (1.8F), −126.6 (52F), −127.8 (1.8F), −133.3 (0.2F), −138.0 (0.2F)

Average value of the number of units (n): 13

Ex. 21 to 32

Production and Evaluation of Substrate Having Surface-Treated Layer

Using the compound, mixture or composition obtained in Ex. 1 to 12, surface treatment of a substrate was carried out as Ex. 21 to 32. In each Ex., a substrate having a surface-treated layer was produced by using each of the following dry coating method and wet coating method. As the substrate, chemically tempered glass was used. With respect to the obtained substrates having a surface-treated layer, evaluations were carried out by the following methods. The results are shown in Table 2.

(Dry Coating Method)

The dry coating method was carried out by using a vacuum deposition apparatus (VTR-350M manufactured by ULVAC, Inc.) (vacuum deposition method). 0.5 g of the compound, mixture or composition obtained in Ex. 1 to 12, was filled in a boat made of molybdenum in the vacuum deposition apparatus, and inside of the vacuum deposition apparatus was evacuated to at most 1×10$^{-3}$ Pa. The boat having the compound, mixture or composition disposed was heated at a heating rate of at most 10° C./min, and at the time when the deposition rate measured by a quartz film thickness meter exceeded 1 nm/sec, a shutter was opened to initiate film deposition on the substrate surface. At the time when the film thickness reached about 50 nm, the shutter was closed to complete film deposition on the substrate surface. The substrate on which the compound, mixture or composition was deposited was subjected to heat treatment at 200° C. for 30 minutes and then washed with AK-225 (tradename, manufactured by Asahi Glass Company, Limited) which is a fluorinated solvent, to obtain a substrate having a surface-treated layer.

(Wet Coating Method)

The compound, mixture or composition obtained in Ex. 1 to 12 and Novec-7200 (tradename, manufactured by 3M) as a solvent were mixed to prepare a coating liquid having a solid content concentration of 0.05 mass %. The substrate was dipped in the coating liquid (dip coating method), left to stand for 30 minutes and then pulled out. The substrate was dried at 200° C. for 30 minutes and washed with AK-225 (tradename, manufactured by Asahi Glass Company, Limited) which is a fluorinated solvent, to obtain a substrate having a surface-treated layer.

(Evaluation Methods)
<Method for Measuring Water Contact Angle and n-Hexadecane Contact Angle>

The contact angle of about 2 μL of distilled water or n-hexadecane placed on the surface-treated surface of the substrate having a surface-treated layer was measured by a contact angle measuring apparatus DM-500 (manufactured by Kyowa Interface Science Co., Ltd.). Measurement was carried out on different five positions on the surface-treated surface of the substrate, and their average value was calculated. To calculate the contact angle, 2θ method was employed.

<Initial Water and n-Hexadecane Contact Angles>

With respect to the substrate surface-treated by each of the dry coating method and the wet coating method (the substrate having a surface-treated layer), the initial water contact angle and the initial n-hexadecane contact angle were measured by the above measurement method.

<Abrasion Resistance>

With respect to the substrate having a surface-treated layer produced in each of Ex. 21 to 32, in accordance with JIS L0849, by means of a reciprocal traverse tester (manufactured by KNT), a cellulose nonwoven fabric (BEMCOT M-3, manufactured by Asahi Kasei Corporation) was reciprocated 100,000 times under a load of 1 kg, whereupon the water contact angle and the n-hexadecane contact angle were measured.

The smaller the decrease of the water repellency (water contact angle) and the oil repellency (n-hexadecane contact angle) when the number of abrasion times was increased, the smaller the decrease in the performance by abrasion, and the better the abrasion resistance.

<Fingerprint Stain Removability>

An artificial fingerprint liquid (a liquid composed of oleic acid and squalene) was deposited on a flat surface of a silicon rubber stopper, and then, excess oil was wiped off with a nonwoven fabric (BEMCOT M-3, manufactured by Asahi Kasei Corporation) to prepare a fingerprint stamp. On a substrate having a surface-treated layer in each of Ex. 21 to 32, the fingerprint stamp was placed and pressed under a load of 1 kg for 10 seconds. At that time, the haze at the portion where the fingerprint was stamped, was measured by a haze meter (manufactured by Toyo Seiki Co., Ltd.). The value at that time was taken as the initial value. Then, at the portion where the fingerprint was stamped, by means of a reciprocal traverse tester (manufactured by KNT) having tissue paper attached, wiping was carried out under a load of 500 g. The haze value was measured after every wiping reciprocation, and if it reached a numerical value where the haze is no longer visually observed, within 10 wiping reciprocations, such a case was taken as "acceptable".

TABLE 1

| Ex. No. | | No. | Group (α) | Group (β) | Group A | Group B | Number average molecular weight |
|---|---|---|---|---|---|---|---|
| Ex. 1 | Composition (A) | 1-3a-1i | $-CF_2CF_2O-$ | $-CF_2CF_2CF_2CF_2O-$ | $CF_3CF_2-$ | Formula (2-3) | 2,900 |
| Ex. 2 | Composition (B) | 1-3a-1ii | $-CF_2CF_2O-$ | $-CF_2CF_2CF_2CF_2O-$ | $CF_3CF_2-$ | Formula (2-3) | 4,900 |
| Ex. 3 | Mixture (C) | 1-1Ha-1i 1-2Ha-1i | $-CF_2CF_2O-$ | $-CF_2CF_2CF_2CF_2O-$ | $CF_3CF_2-$ | Formula (2-1) Formula (2-2) | 2,900 |
| Ex. 4 | Mixture (D) | 1-1Ha-1ii 1-2Ha-1ii | $-CF_2CF_2O-$ | $-CF_2CF_2CF_2CF_2O-$ | $CF_3CF_2-$ | Formula (2-1) Formula (2-2) | 4,900 |
| Ex. 5 | Compound (E) | 1-1Fa-1 | $-CF_2CF_2O-$ | $-CF_2CF_2CF_2CF_2O-$ | $CF_3CF_2-$ | Formula (2-1) | 3,000 |
| Ex. 6 | Composition (F) | 1-3a-2 | $-CF_2CF_2O-$ | $-CF_2CF_2CF_2CF_2O-$ | $CF_3-$ | Formula (2-3) | 2,900 |
| Ex. 7 | Mixture (G) | 1-1Ha-2 1-2Ha-2 | $-CF_2CF_2O-$ | $-CF_2CF_2CF_2CF_2O-$ | $CF_3-$ | Formula (2-1) Formula (2-2) | 4,900 |
| Ex. 8 | Composition (H) | 1-3b-1 | $-CF_2CF_2O-$ | $-CF_2CF_2CF_2OCF_2CF_2CF_2O-$* | $CF_3CF_2-$ | Formula (2-3) | 3,000 |
| Ex. 9 | Mixture (I) | 1-1Hb-1 1-2Hb-1 | $-CF_2CF_2O-$ | $-CF_2CF_2CF_2OCF_2CF_2CF_2O-$* | $CF_3CF_2-$ | Formula (2-1) Formula (2-2) | 3,000 |
| Ex. 10 | Compound (J) | — | $(CF_2O)$ $(CF_2CF_2O)$ | — | | | |
| Ex. 11 | Mixture (K) | 1-4a-1 17a-1 18a-1 | $-CF_2CF_2O-$ | $-CF_2CF_2CF_2CF_2O-$ | $CF_3-$ | Formula (2-4) Formula (2-7) Formula (2-9) | 4,800 |
| Ex. 12 | Mixture (L) | 1-5a-1 18a-1 | $-CF_2CF_2O-$ | $-CF_2CF_2CF_2CF_2O-$ | $CF_3-$ | Formula (2-5) Formula (2-9) | 4,800 |

*In Ex. 8 and 9, the column for group (β) represents that two groups (β) are linked.

TABLE 2

| | | Dry coating method | | | | | Wet coating method | | | | |
|---|---|---|---|---|---|---|---|---|---|---|---|
| | | Water contact angle (degree) | | n-Hexadecane contact angle (dgree) | | | Water contact angle (degree) | | n-Hexadecane contact angle (dgree) | | |
| Ex. No. | Fluorinated ether compound, mixture or composition | Initial | After 100,000 abrasion times | Initial | After 100,000 abrasion times | Fingerprint removability | Initial | After 100,000 abrasion times | Initial | After 100,000 abrasion times | Fingerprint removability |
| Ex. 21 | (A) | 114.4 | 111.5 | 65.5 | 64.2 | Acceptable | 112.8 | 102.0 | 67.2 | 60.2 | Acceptable |
| Ex. 22 | (B) | 112.2 | 111.0 | 67.8 | 66.6 | Acceptable | 112.8 | 106.9 | 68.8 | 65.0 | Acceptable |
| Ex. 23 | (C) | 111.0 | 108.8 | 66.9 | 66.5 | Acceptable | 111.1 | 108.7 | 66.1 | 65.9 | Acceptable |

TABLE 2-continued

| | | Dry coating method | | | | | Wet coating method | | | | |
|---|---|---|---|---|---|---|---|---|---|---|---|
| | | Water contact angle (degree) | | n-Hexadecane contact angle (dgree) | | | Water contact angle (degree) | | n-Hexadecane contact angle (dgree) | | |
| Ex. No. | Fluorinated ether compound, mixture or composition | Initial | After 100,000 abrasion times | Initial | After 100,000 abrasion times | Fingerprint removability | Initial | After 100,000 abrasion times | Initial | After 100,000 abrasion times | Fingerprint removability |
| Ex. 24 | (D) | 113.9 | 113.5 | 67.0 | 65.9 | Acceptable | 112.5 | 114.7 | 67.0 | 66.7 | Acceptable |
| Ex. 25 | (E) | 112.9 | 107.9 | 65.6 | 63.9 | Acceptable | 111.9 | 109.2 | 66.8 | 65.3 | Acceptable |
| Ex. 26 | (F) | 111.1 | 110.0 | 67.4 | 67.5 | Acceptable | 112.5 | 105.2 | 69.2 | 64.2 | Acceptable |
| Ex. 27 | (G) | 110.6 | 111.1 | 67.6 | 69.0 | Acceptable | 112.1 | 110.7 | 67.4 | 67.2 | Acceptable |
| Ex. 28 | (H) | 116.8 | 115.0 | 66.5 | 65.9 | Acceptable | 113.6 | 101.2 | 67.6 | 63.5 | Acceptable |
| Ex. 29 | (I) | 115.7 | 110.9 | 66.9 | 63.3 | Acceptable | 112.9 | 105.1 | 68.6 | 64.9 | Acceptable |
| Ex. 30 | (J) | 110.8 | 102.0 | 66.6 | 60.9 | Acceptable | 111.3 | 112.9 | 66.2 | 66.6 | Acceptable |
| Ex. 31 | (K) | 113.4 | 110.9 | 68.6 | 65.4 | Acceptable | 113.7 | 106.0 | 67.4 | 61.3 | Acceptable |
| Ex. 32 | (L) | 112.1 | 110.0 | 66.5 | 66.0 | Acceptable | 111.7 | 103.7 | 65.3 | 63.3 | Acceptable |

As the results in Table 2 show, the substrate having a surface-treated layer in each of Ex. 21 to 29, 31 and 32, wherein the present compound was used, was excellent in the initial water contact angle and n-hexadecane contact angle, and particularly in the case of the substrate having a surface-treated layer formed by the dry coating method, the decrease in the contact angle was small even when abraded 100,000 times. It has been confirmed that the present compound having groups ($\alpha$) and ($\beta$) is capable of imparting good initial water/oil repellency to the surface of a substrate and at the same time, has good fingerprint stain removability, is excellent in abrasion resistance whereby the water/oil repellency is less likely to be lowered even by repeated abrasion, and can be efficiently produced.

From the results in Ex. 21 and 22, it has been confirmed that the decrease in the contact angle is smaller in Ex. 22 wherein the present compound having a higher number average molecular weight was used.

The substrate having a surface-treated layer in Ex. 30 wherein a fluorinated ether compound having ($CF_2O$) and ($CF_2CF_2O$) was used, was slightly poor in the initial water contact angle and n-hexadecane contact angle, and in the case of the substrate having a surface-treated layer formed by the dry coating method, the decrease in the contact angle by abrasion was large.

INDUSTRIAL APPLICABILITY

The fluorinated ether compound of the present invention is useful for surface treatment to impart water/oil repellency to the surface of a substrate such as a member constituting a surface to be touched with a finger, of a touch panel.

This application is a continuation of PCT Application No. PCT/JP2013/052943, filed on Feb. 7, 2013, which is based upon and claims the benefit of priority from Japanese Patent Application No. 2012-032784 filed on Feb. 17, 2012 and Japanese Patent Application No. 2012-224262 filed on Oct. 9, 2012. The contents of those applications are incorporated herein by reference in their entireties.

What is claimed is:

1. A fluorinated ether compound which has a poly(oxyperfluoroalkylene) chain made of at least two units linked to one another, and which has a hydrolysable silyl group on at least one terminal of the poly(oxyperfluoroalkylene) chain via a linking group, wherein each unit is a poly(oxyperfluoroalkylene) group comprising one to three groups ($\alpha$) made of at least one type of a $C_{1-2}$ oxyperfluoroalkylene group and one to three groups ($\beta$) made of at least one type of a $C_{3-6}$ oxyperfluoroalkylene group.

2. The fluorinated ether compound according to claim 1, wherein the groups ($\alpha$) and ($\beta$) are arranged so that in each unit, one end is the group ($\alpha$) and the other end is the group ($\beta$).

3. The fluorinated ether compound according to claim 1, wherein a $C_{1-6}$ perfluoroalkyl group, or a $C_{2-6}$ perfluoroalkyl group having an etheric oxygen atom, is bonded via an oxygen atom to the carbon atom at one end of the poly(oxyperfluoroalkylene) chain, and the hydrolysable silyl group is bonded via the linking group to the oxygen atom at the other end of the poly(oxyperfluoroalkylene) chain.

4. The fluorinated ether compound according to claim 3, wherein the carbon atom at one end of the poly(oxyperfluoroalkylene) chain is a carbon atom of the group ($\alpha$), and the oxygen atom at the other end of the poly(oxyperfluoroalkylene) chain is an oxygen atom of the group ($\beta$).

5. The fluorinated ether compound according to claim 1, which has a number average molecular weight of from 2,000 to 10,000.

6. The fluorinated ether compound according to claim 1, wherein the group ($\beta$) is ($CF_2CF_2CF_2CF_2O$).

7. A fluorinated ether composition containing at least 95 mass % of the fluorinated ether compound as defined in claim 1.

8. A substrate having a surface-treated layer, obtained by treatment with the fluorinated ether composition as defined in claim 7.

9. A touch panel having, on its input screen, the substrate having a surface-treated layer, obtained by treatment with the fluorinated ether composition as defined in claim 7.

10. A coating liquid comprising the fluorinated ether compound as defined in claim 1, and a medium.

11. The coating liquid according to claim 10, wherein the medium contains at least one organic solvent selected from the group consisting of a fluorinated alkane, a fluorinated aromatic compound and a fluoroalkyl ether.

12. A method for producing a substrate having a surface-treated layer, which comprises a step of applying the coating liquid as defined in claim 10 to the surface of a substrate, followed by dying.

13. The method for producing a substrate having a surface-treated layer according to claim 12, wherein the method of applying the coating liquid to the surface of the substrate is a spin coating method, a wipe coating method, a spray coating method, a squeegee coating method, a dip coating method, a die coating method, an ink jet method, a flow coating method, a roll coating method, a casting method, a Langmuir-Blodgett method or a gravure coating method.

14. The method for producing a substrate having a surface-treated layer according to claim 12, wherein the material for the substrate is a metal, a resin, glass, a ceramic or a composite material thereof.

15. A method for producing a substrate having a surface-treated layer, which comprises a step of applying the fluorinated ether compound as defined in claim 1 or a fluorinated ether composition containing at least 95 mass % of the fluorinated ether compound to the surface of a substrate by vacuum deposition.

16. The method for producing a substrate having a surface-treated layer according to claim 15, wherein the material for the substrate is a metal, a resin, glass, a ceramic or a composite material thereof.

* * * * *